United States Patent
Culler et al.

(10) Patent No.: US 10,844,404 B2
(45) Date of Patent: Nov. 24, 2020

(54) ENGINEERED MICROORGANSIMS AND METHODS FOR IMPROVED CROTYL ALCOHOL PRODUCTION

(71) Applicant: Genomatica, Inc., San Diego, CA (US)

(72) Inventors: Stephanie J. Culler, San Diego, CA (US); Nicholas Eakley, San Diego, CA (US); Kevin Gregory Hoff, San Diego, CA (US); Robin E. Osterhout, San Diego, CA (US); Priti Pharkya, San Diego, CA (US); Erik C. Ralph, San Diego, CA (US); Stephen Van Dien, San Diego, CA (US)

(73) Assignee: Genomatica Inc., San Diego, CA (US)

( * ) Notice: Subject to any disclaimer, the term of this patent is extended or adjusted under 35 U.S.C. 154(b) by 209 days.

(21) Appl. No.: 15/564,327

(22) PCT Filed: Apr. 7, 2016

(86) PCT No.: PCT/US2016/026445
§ 371 (c)(1),
(2) Date: Oct. 4, 2017

(87) PCT Pub. No.: WO2016/164586
PCT Pub. Date: Oct. 13, 2016

(65) Prior Publication Data
US 2018/0135082 A1    May 17, 2018

Related U.S. Application Data

(60) Provisional application No. 62/145,290, filed on Apr. 9, 2015.

(51) Int. Cl.
| | |
|---|---|
| *C12P 5/02* | (2006.01) |
| *C12N 9/04* | (2006.01) |
| *C12N 9/02* | (2006.01) |
| *C12P 7/16* | (2006.01) |
| *C12P 7/04* | (2006.01) |

(52) U.S. Cl.
CPC .............. *C12P 5/026* (2013.01); *C12N 9/001* (2013.01); *C12N 9/0006* (2013.01); *C12P 7/04* (2013.01); *C12P 7/16* (2013.01); *Y02E 50/10* (2013.01)

(58) Field of Classification Search
None
See application file for complete search history.

(56) References Cited

FOREIGN PATENT DOCUMENTS

| WO | 2011/140171 A2 | 11/2011 |
| WO | 2012/106516 A1 | 9/2012 |
| WO | 2013/057194 A1 | 4/2013 |

OTHER PUBLICATIONS

Sommer et al., "Catalytic Modules in Non-Natural Butanol Biosynthesis: Conversion of the Key Intermediate Crotylalcohol to N-Butanol Via a Designed Enzyme Cascade", JSM Biotechnology & Biomedical Engineering, vol. 1, 2010, pp. (1010)-7(1016).
Lan et al., "Microbial Synthesis of N-Butanol, Isobutanol, and Other Higher Alcohols from Diverse Resources", Bioresource Technology, vol. 135, 2013, pp. 339-349.
Muschiol et al., "Cascade Catalysis—Strategies and Challenges En Route to Preparative Synthetic Biology", Chemcomm, vol. 51, Dec. 10, 2014, pp. 5798-5811.
Winkler et al., "Asymmetric Bioreduction of Activated Alkenes to Industrially Relevant Optically Active Compounds", Journal of Biotechnology, vol. 162, 2012, pp. 381-389.
Toogood et al., "New Developments in "Ene"-Reductase Catalysed Biological Hydrogenations", Current Opinion in Chemical Biology, vol. 19, 2014, pp. 107-115.
Song et al., "Improving Alkane Synthesis in *Escherichia coli* Via Metabolic Engineering", Applied Microbiology an Biotechnology, vol. 100, Oct. 17, 2015, pp. 757-767.

*Primary Examiner* — Kagnew H Gebreyesus
(74) *Attorney, Agent, or Firm* — Kagan Binder, PLLC

(57) ABSTRACT

Disclosed are methods and engineered microorganisms that enhance or improve the production of crotyl alcohol. The engineered microorganisms include genetic modifications in alcohol dehydrogenase, alkene reductase or both enzymatic activities. By such genetic modifications, a crotyl alcohol production pathway is provided or improved.

20 Claims, 8 Drawing Sheets

Specification includes a Sequence Listing.

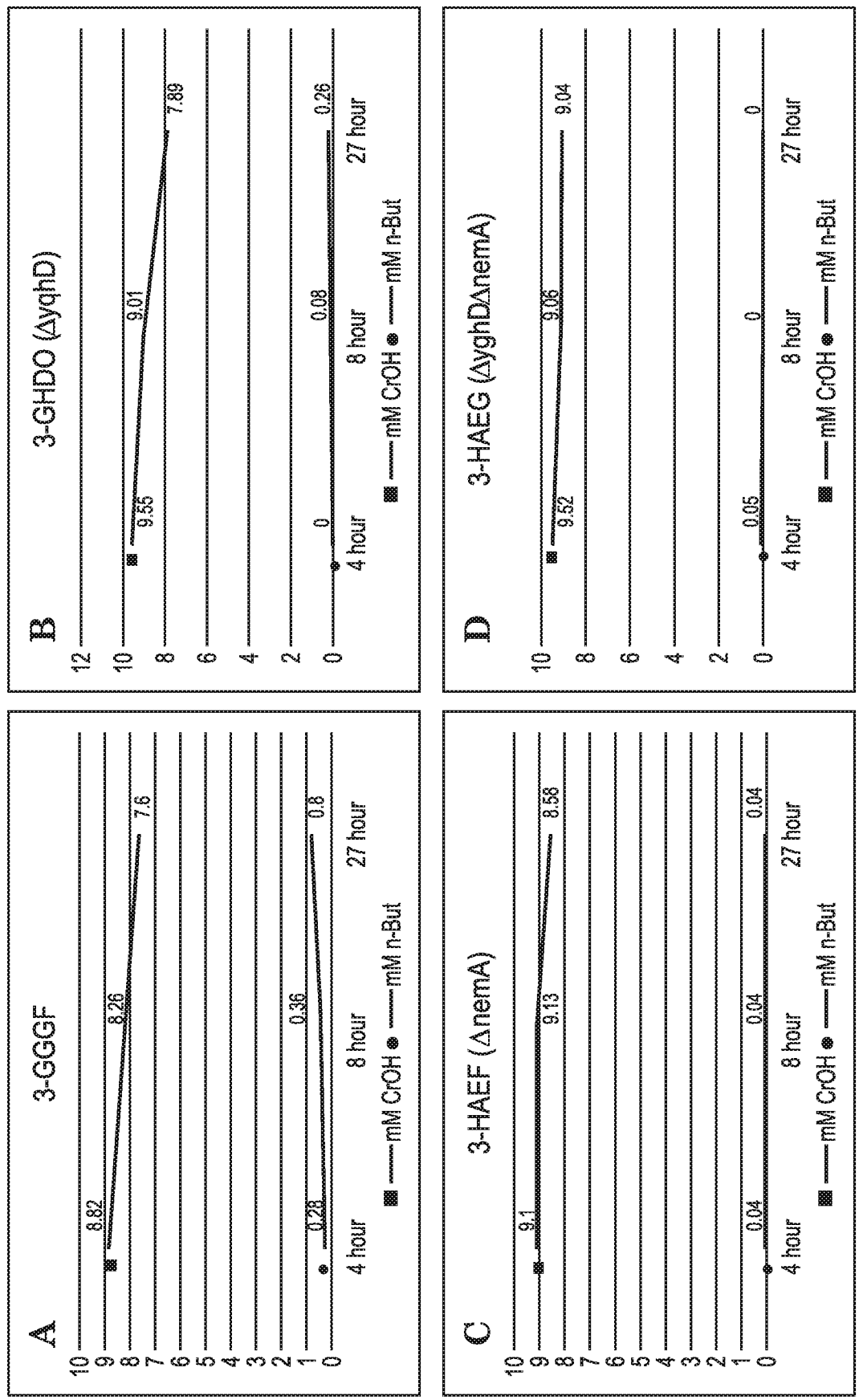
FIG. 6A-D

ENGINEERED MICROORGANSIMS AND METHODS FOR IMPROVED CROTYL ALCOHOL PRODUCTION

PRIORITY CLAIM

This application claims priority to International Application No. PCT/US2016/026445, filed on Apr. 7, 2016, which claims the benefit of U.S. Provisional Patent Application Ser. No. 62/145,290 filed Apr. 9, 2015, the disclosures of which are incorporated in their entirety herein by reference.

The entire contents of the ASCII text file entitled GNO0025WO Sequence Listing_ST25 created on Mar. 29, 2016 and having a size of 31 kilobytes is incorporated herein by reference.

BACKGROUND

Crotyl alcohol, also referred to as crotonyl alcohol, crotonol or but-2-en-1-ol, is an unsaturated alcohol of the formula $C_4H_8O$ and shown in FIG. 1. Crotyl alcohol is a valuable chemical intermediate serving as a precursor to alkenes including 1,3-butadiene, crotyl halides, esters, and ethers, which in turn are chemical intermediates in the production of polymers, fine chemicals, agricultural chemicals, and pharmaceuticals.

Engineered microorganisms that produce increased crotyl alcohol are attractive alternatives to petroleum-based productions. But when such alcohols are produced by the cells and released they can accumulate into the media during culturing. Changes in the culture media conditions can affect a microorganism's growth and viability because microbes, such as bacteria, generally have low alcohol tolerance.

Alcohol removal from the media during culturing is one way to address this problem. But such removal processes can be expensive and inefficient. Another approach is to use natural bacterial isolates that demonstrate tolerance to higher alcohol levels. Such strains, however, are generally not suitable for industrial production or engineering.

SUMMARY OF THE INVENTION

Disclosed are methods and engineered microorganisms that produce crotyl alcohol as a bioproduct or as an intermediate for the production of other bioproducts.

In one embodiment, a method is provided for producing a bioproduct using an engineered microorganism, where crotyl alcohol is the bioproduct, or crotyl alcohol is an intermediate in a bioproduct pathway (e.g. 1,3-butadiene, 1,3-butanediol, methyl vinyl carbinol), the method comprising:
culturing the engineered microorganism under conditions resulting in crotyl alcohol production or use of crotyl alcohol as the intermediate in a bioproduct pathway resulting in bioproduct production, wherein the engineered microorganism comprises at least one genetic modification causing partial or complete loss of activity in (a) an alcohol dehydrogenase (ADH) that converts crotyl alcohol to crotonaldehyde, (b) an ADH that converts butyraldehyde to butanol, or (c) an alkene reductase that converts crotonaldehyde to butyraldehyde or any combination of (a), (b) and (c).

In some embodiments, the microorganism further comprises at least one exogenous nucleic acid encoding an enzyme of a bioproduct pathway, where the bioproduct pathway is a crotyl alcohol pathway or uses a crotyl alcohol as an intermediate in the bioproduct pathway.

In another embodiment, an engineered microorganism is disclosed comprising at least one genetic modification causing partial or complete loss of activity in (a) an alcohol dehydrogenase (ADH) that converts crotyl alcohol to crotonaldehyde, (b) an ADH that converts butyraldehyde to butanol, or (c) an alkene reductase that converts crotonaldehyde to butyraldehyde or any combination of (a), (b) and (c) and at least one exogenous nucleic acid encoding an enzyme of a bioproduct pathway, where the bioproduct pathway is a crotyl alcohol pathway or uses crotyl alcohol as an intermediate in the bioproduct pathway.

In still other embodiments, a method is provided for producing a bioproduct using an engineered microorganism, where crotyl alcohol is the bioproduct, or crotyl alcohol is an intermediate in a bioproduct pathway (e.g. 1,3-butadiene, 1,3-butanediol, methyl vinyl carbinol), the method comprising:
providing an engineered microorganism having at least one genetic modification causing partial or complete loss of activity in in (a) an alcohol dehydrogenase (ADH) that converts crotyl alcohol to crotonaldehyde, (b) an ADH that converts butyraldehyde to butanol, or (c) an alkene reductase that converts crotonaldehyde to butyraldehyde or any combination of (a), (b) and (c); and
culturing the engineered microorganism under conditions resulting in crotyl alcohol production or use of crotyl alcohol as the intermediate in a bioproduct pathway resulting in bioproduct production.

In some embodiments, the alcohol dehydrogenases and alkene reductases subject to the partial or complete loss of activity are native to the microorganism and the alcohol dehydrogenase is capable of converting crotyl alcohol to crotonaldehyde and/or converting butyraldehyde to butanol, and the alkene reductase is capable of converting crotonaldehyde to butyraldehyde. These native activities have been identified as undesirable activities when they compete with desirable enzyme activities that comprise a pathway to crotyl alcohol or a crotyl alcohol-derived bioproduct.

The microorganism can be further genetically modified to increase activity of an enzyme converting crotonaldehyde to crotyl alcohol, e.g., a crotonaldehyde reductase (alcohol forming), particularly where crotonaldehyde is a by-product and not a bioproduct pathway intermediate.

Such disclosed methods and engineered microorganisms allow for growth on crotyl alcohol levels higher than microorganisms without the genetic modifications. Such microorganisms can also produce significantly more crotyl alcohol. In addition, the disclosed methods and microorganisms can increase the efficiency of crotyl alcohol yields and/or decrease process costs by reducing or eliminating crotyl alcohol into undesirable or wasteful pathways.

BRIEF DESCRIPTION OF THE DRAWINGS

FIGS. 6A-D show crotyl alcohol and butanol measurements in various nemA and yqhD deleted strains (3-GGGF, 3-GHDO, 3-HAEF, 3-HAEG).

DETAILED DESCRIPTION

Figure 1:
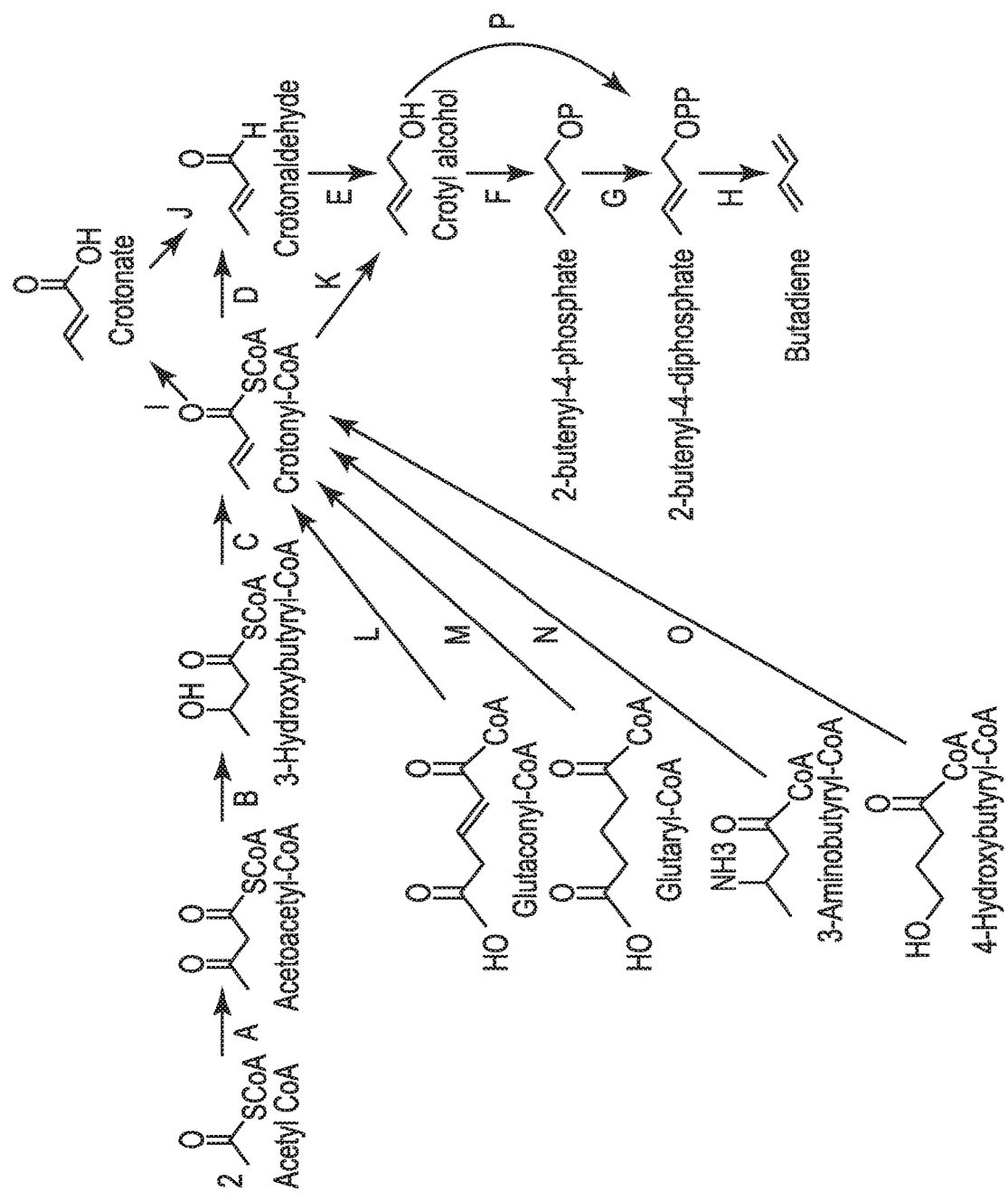
FIG. 1. shows exemplary pathways for production of crotyl alcohol and butadiene from acetyl-CoA, glutaconyl-CoA, glutaryl-CoA, 3-aminobutyryl-CoA or 4-hydroxybutyryl-CoA via crotyl alcohol. Enzymes for transformation of the identified substrates to products include: A. acetyl-CoA:acetyl-CoA acyltransferase, B. acetoacetyl-CoA reductase, C. 3-hydroxybutyryl-CoA dehydratase, D. crotonyl-CoA reductase (aldehyde forming), E. crotonaldehyde reductase (alcohol forming), F. crotyl alcohol kinase, G. 2-butenyl-4-phosphate kinase, H. butadiene synthase, I. crotonyl-CoA hydrolase, synthetase, transferase, J. crotonate reductase, K. crotonyl-CoA reductase (alcohol forming), L. glutaconyl- CoA decarboxylase, M., glutaryl-CoA dehydrogenase, N. 3-aminobutyryl-CoA deaminase, O. 4-hydroxybutyryl-CoA dehydratase, P. crotyl alcohol diphosphokinase.

The embodiments of the invention described here are not intended to be exhaustive or to limit the description to the precise forms disclosed in the following detailed description. Rather, the embodiments are chosen and described so that others skilled in the art can appreciate and understand the principles and practices of the description.

All publications and patents mentioned here are hereby incorporated by reference in their entirety. The publications and patents disclosed here are provided solely for their disclosure.

The term "alcohol dehydrogenase" (also referred to as ADH) as used here refers to enzymes that can convert crotyl alcohol to crotonaldehyde and/or butyraldehyde to butanol, and includes those classified as EC 1.1.1. An enzyme converting crotyl alcohol to crotonaldehyde is also referred to here as a crotyl alcohol dehydrogenase (crotyl ADH). An alcohol dehydrogenase converting butyraldehyde to butanol is also referred to here as a butyraldehyde reductase (alcohol forming).

The term "alkene reductase" refers to an enzyme that can convert crotonaldehyde to butyraldehyde.

The term "bioproduction", as used here refers to microbial synthesis. The terms "production" and "biosynthesis" are used interchangeably when referring to microbial synthesis of a desired or referenced substance or product.

The term "engineered" refers to a microbial organism or microorganism has at least one genetic modification not normally found in a naturally occurring strain, wild-type strain or the parental host strain of the referenced species.

The term "exogenous" as it is used here refers to the referenced molecule or the referenced activity that is introduced into a host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity or bioproduct, the term refers to an activity that is introduced into the parental host organism. The source can be, for example, a homologous or heterologous encoding nucleic acid that expresses the referenced activity following introduction into the parental host microbial organism. Accordingly, exogenous includes genetic modification to a regulatory region of a native gene or to a regulatory protein of a native gene that results in expression of that native gene or its encoded enzyme that is different than in the absence of that modification. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of a disclosed encoding nucleic acid can utilize either or both a heterologous or homologous encoding nucleic acid.

The term "genetic modifications" as used here refers to an alteration in which expression of nucleic acids, polypeptides that are deleted or introduced to encode or express metabolic polypeptides, enzymes, other nucleic acid additions, nucleic acid deletions and/or other functional disruption of the microbial organism's genetic material. Such modifications for example may be made in, coding regions and functional fragments thereof, for heterologous, homologous or both heterologous and homologous polypeptides for the referenced species. Additional modifications include, for example, non-coding regulatory regions in which the modifications alter expression of a gene or operon. The term "genetic alteration" is used interchangeably with genetic modification.

The term "metabolic modification" refers to a biochemical reaction that is altered from its naturally occurring state. Therefore, engineered microorganisms can have genetic modifications to nucleic acids encoding metabolic polypeptides, or functional fragments thereof.

The terms "microbial," "microbial organism" or "microorganism" refers to organisms that exist as microscopic cells and encompass prokaryotic or eukaryotic cells or organisms having a microscopic size and includes bacteria, archaea and eubacteria of all species as well as eukaryotic microorganisms such as yeast and fungi. The term also includes cells of any species that can be cultured for the production of a bioproduct.

The term "parental microbial organism," or grammatical equivalents thereof (and including parent host microorganism or host microorganism) when used in the context of a genetic modification, is understood to mean a parent microorganism or strain in which the particular genetic modification has not been made but otherwise has the same genetic makeup. For example, if a strain of microbial organism is used to make a genetic modification that increases expression of a gene product, the parent strain would be the starting strain into which the heterologous gene is introduced. Similarly, a parent microbial organism in which a genetic modification has been made to decrease expression, such as a gene disruption or gene deletion, the parent microbial organism would have the same genetic background except for the gene disruption or deletion. However, it is understood that a parent microbial organism can differ by more than one genetic modification, either gene addition and/or disruption, depending on whether a single or multiple genetic modifications are being considered. One skilled in the art will readily understand the meaning of such a parent microbial organism in that the microorganism is considered to be an appropriate control, as understood in the art, for observing the effect of one or more genetic modifications.

The term, "partial loss," "reduced activity," and the like refers to a microorganism's enzyme or an isolated enzyme that exhibits a lower activity level than that measured in a parent microbial organism or its native enzyme. This term also can include elimination of that enzymatic activity.

Disclosed are engineered microorganisms with genetic modifications to ADH enzymatic activity, alkene reductase enzymatic activity or both. Such engineered microorganisms are capable of accumulating greater crotyl alcohol amounts (e.g. titers), having greater availability of crotyl alcohol, as well as capable of growing on higher crotyl alcohol levels compared to a parental host strain or microorganisms without the disclosed genetic modifications. Such engineered microorganisms may be used for the fermentation production of crotyl alcohol. The engineered microorganisms may also be useful in providing improved crotyl alcohol pathways and other bioproduct pathways via crotyl alcohol as an intermediate. In addition, the disclosed methods and microorganisms can increase the efficiency of crotyl alcohol yields and/or decrease process costs by reducing or eliminating undesirable or wasteful pathways that divert crotyl alcohol into unwanted metabolic products or intermediates, some of which may adversely impact the microorganism's health. For example, by having greater crotyl alcohol availability compared to the parental strain, more crotyl alcohol can be enzymatically converted to a bioproduct of interest, such as butadiene, 1,3-butanediol or methyl vinyl carbinol or to an intermediate to a bioproduct of interest. The cells are cultured in suitable medium using methods and media known in the art.

Exemplary microorganisms that may serve as the parental host microbial organism to be engineered include, for example, bacteria, yeast, fungus or any of a variety of other microorganisms applicable to fermentation processes, including methylotophs or microbes engineered to be methylotrophs. Exemplary bacteria include the genus selected from *Acinetobacter, Escherichia, Klebsiella, Anaerobiospirillum, Actinobacillus, Castellaniella, Mannheimia, Bacillus, Zymomonas, Lactococcus, Lactobacillus, Streptomyces, Clostridium, Pseudomonas, Thauera* and *Zymomonas*.

Other exemplary bacteria include species selected from *Escherichia coli, Klebsiella oxytoca, Anaerobiospirillum succiniciproducens, Actinobacillus succinogenes, Castellaniella caeni, Castellaniella daejeonensis, Castellaniella defragrans, Castellaniella denitrificans, Castellaniella ginsengisoli, Castellaniella hirudinis, Mannheimia succiniciproducens, Rhizobium etli, Bacillus subtilis, Bacillus methanolicus, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens, Thauera aminoaromatica, Thauera aromatica, Thauera butanivorans, Thauera chlorobenzoica, Thauera humireducens, Thauera linaloolentis, Thauera mechemichensis, Thauera phenylacetica, Thauera selenatis, Thauera terpenica* and *Pseudomonas putida*.

Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae, Yarrowia lipolytica*, and the like.

*E. coli* is a particularly useful parental host organism since it is a well characterized microbial organism suitable for genetic engineering. Other particularly useful host microorganisms include yeast such as *Saccharomyces cerevisiae*. It is understood that any suitable microorganism can be used to introduce metabolic and/or genetic modifications to produce an engineered microorganism, which engineered microorganism is capable of producing a desired bioproduct. In some embodiments, *E. coli* include strains *E. coli* Str K-12 substr. MG1655 and *E. coli* ATCC 8739 variant. In one embodiment the the host organism is not *Bacillus subtilis*.

Alcohol Dehydrogenases

In some embodiments, the genes encoding ADH activity are deleted or disrupted. The disclosed ADH enzymes targeted for gene deletion or disruption can also include those ADH enzymes that use reduced nicotinamide adenine dinucleotide (NADH) and/or NADPH as an electron donor.

Figure 3:
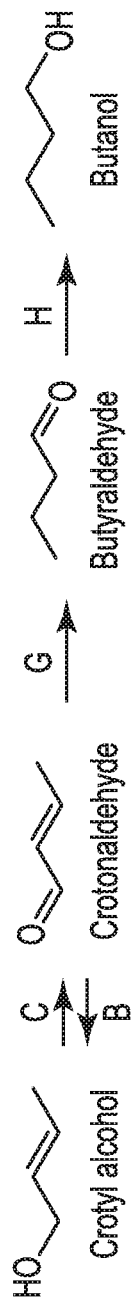
FIG. 3 shows reactions for conversion of crotyl alcohol to by-products (Step C, G and/or H) and for conversion of a by-product crotonaldehyde to crotyl alcohol (Step B). The enzymes for transforming the identified substrates include, B. crotonaldehyde reductase (alcohol forming), also referred to as an aldehyde reductase (alcohol forming), C. crotyl alcohol dehydrogenase, G. crotonaldehyde reductase (also referred to as an alkene reductase), H. butyraldehyde reductase (alcohol forming).

In some embodiments, increase in the amount of crotyl alcohol and/or tolerance to crotyl alcohol can be caused by the disruption of the disclosed ADH genes that encode for enzymes which otherwise catalyzes the conversion of crotyl alcohol to crotonaldehyde and/or butyraldehyde to butanol. Deletion in the ADH activity results in reduction or partial or full loss of ADH activity and as shown in FIG. 3 as enzyme C. Deletion of ADH (e.g. as shown as C and/or H) drives the process towards crotyl alcohol. In some embodiments, the ADH enzymes to be deleted are native or endogenous to the engineered microorganism. The native activities may be identified as undesirable activities when they compete with desirable enzyme activities that include crotyl alcohol or crotyl alcohol-derived bioproducts.

In some embodiments, the enzymes for converting crotyl alcohol to crotonaldehyde and/or butyraldehyde to butanol are the same. In other embodiments, the enzymes for converting crotyl alcohol to crotonaldehyde are different from the enzymes for converting butyraldehyde to butanol.

Table 1 lists exemplary ADH genes that can be disrupted or deleted.

TABLE 1

| Gene | GenBank ID | GI Number | Organism |
| --- | --- | --- | --- |
| alrA | BAB12273.1 | 9967138 | cinetobacter sp. Strain M-1 |
| ADH2 | NP_014032.1 | 6323961 | Saccharomyces cerevisiae |
| yqhD | NP_417484.1 | 16130909 | Escherichia coli |
| bdh I | NP_349892.1 | 15896543 | Clostridium acetobutylicum |
| bdh II | NP_349891.1 | 15896542 | Clostridium acetobutylicum |
| adhA | YP_162971.1 | 56552132 | Zymomonas mobilis |
| Cbei_2181 | YP_001309304.1 | 150017050 | Clostridium beijerinckii NCIMB 8052 |

Other ADH genes that can be disrupted or deleted include ADH enzymes active on allyl alcohols can also be suitable for oxidizing crotyl alcohol to crotonaldehyde (see FIG. 3, enzyme C). An exemplary allyl alcohol dehydrogenase is the NtRed-1 enzyme from *Nicotiana tabacum* (Matsushima et al, Bioorg. Chem. 36: 23-8 (2008)). A similar enzyme has been characterized in *Pseudomonas putida* MB1 but the enzyme has not been associated with a gene to date (Malone et al, Appl. Environ. Microbiol 65: 2622-30 (1999)). Yet another allyl alcohol dehydrogenase is the geraniol dehydrogenase enzymes of *Castellaniella defragrans, Carpoglyphus lactis* and *Ocimum basilicum* (Lueddeke et al, AEM 78:2128-36 (2012)). Alcohol dehydrogenase enzymes with broad substrate specificity are also applicable here, such as include alrA encoding a medium-chain alcohol dehydrogenase for C2-C14 (Tani et al., Appl. Environ. Microbiol. 66:5231-5235 (2000)), yqhD, yahK, adhE and fucO from *E. coli* (Sulzenbacher et al., J Mol Biol 342:489-502 (2004)), and bdh I and bdh II from *C. acetobutylicum* which converts butyryaldehyde into butanol (Walter et al, J. Bacteriol. 174:7149-7158 (1992)). YqhD of *E. coli* catalyzes the reduction of a wide range of aldehydes using NADPH as the cofactor, with a preference for chain lengths longer than C(3) (Sulzenbacher et al, J Mol Biol 342:489-502 (2004); Perez et al., J Biol. Chem. 283:7346-7353 (2008)). The adhA gene product from *Zymomonas mobilis* has been demonstrated to have activity on a number of aldehydes including formaldehyde, acetaldehyde, propionaldehyde, butyraldehyde, and acrolein (Kinoshita et al., App. Microbiol. Biotechnol. 22:249-254 (1985)).

Other ADH genes that can be disrupted or deleted include those listed in Table 2.

TABLE 2

| Gene | GenBank Accession No. | GI No. | Organism |
| --- | --- | --- | --- |
| MDR | BAM52497.1 | 407959257 | *Synechocystis* sp. PCC 6803 |
| NT-RED1 | BAA89423 | 6692816 | *Nicotiana tabacum* |
| geoA | CCF55024.1 | 372099287 | *Castellaniella defragrans* |
| GEDH1 | Q2KNL6.1 | 122200955 | *Ocimum basilicum* |
| GEDH | BAG32342.1 | 188219500 | *Carpoglyphus lactis* |
| alrA | BAB12273.1 | 9967138 | *Acinetobacter* sp. strain M-1 |
| ADH2 | NP_014032.1 | 6323961 | *Saccharomyces cerevisiae* |
| fucO | NP_417279.1 | 16130706 | *Escherichia coli* |
| yqhD | NP_417484.1 | 16130909 | *Escherichia coli* |
| yahK | P75691.1 | 2492774 | *Escherichia coli* |
| adhE | NP_415757.1 | 16129202 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |
| Bdh | BAF45463.1 | 124221917 | *Clostridium saccharoperbutylacetonicum* |

Additional ADH enzymes that can be targeted for gene disruption or deletion can be identified based on sequence homologies to the disclosed ADH sequences. In some embodiments, the ADH enzymes include ADH enzymes having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity to the polypeptide or polynucleotide sequence of full length protein sequences in SEQ ID NOs: 11-14, shown in Table 5. Exemplary deletions are shown in SEQ ID NOs: 1-4.

The disclosed ADH enzymes can convert crotyl alcohol to crotonaldehyde and/or butyraldehyde to butanol. In some embodiments, genetic modifications (e.g. deletions or disruptions) to ADHs cause partial or complete loss of ADH activity. In some embodiments, deletion of the ADH genes or activity is deletions of the native genes or enzymes. In still other embodiments, deletion of the native ADH genes encoding ADH activity that can convert crotyl alcohol to crotonaldehyde and/or butyraldehyde to butanol. In some embodiments, the deletions in adh genes include deletions in at least one, two, three, four or five adh genes. In some embodiments, the deletions are deletions in the *E. coli*-encoded adh genes. In other embodiments, the deletions are to one or more sequences as disclosed here as SEQ ID NOs: 1-4 and shown in Table 5.

ADH enzymes that may be modified include activity encoded by, for example, the genes adhE, adhP, yqhD, yahK. In some embodiments, the microorganisms may include deletions or disruptions in the adhE, adhP, yqhD, yahK, genes or combinations thereof. For example, the genetic modifications may include genetic deletions to single genes and denoted as ΔadhE, ΔadhP, ΔyqhD and ΔyahK. The delta symbol denotes a gene deletion. The deletions can include multiple deletions such as to more than one deletion, two, three or four deletions. For example, two deletions in the desired adh gene can be denoted as (ΔadhEΔadhP), (ΔadhEΔadhP), (ΔadhEΔyqhD), and (ΔadhEΔyahK); three deletions in the desired adh genes are denoted as (ΔadhEΔadhPΔyqhD), (ΔadhEΔadhPΔyahK), and four deletions in the desired adh genes are denoted as (ΔadhEΔadhPΔyqhDΔyahK). Such genetic deletions to the disclosed adh genes, polynucleotides and/or polypeptides result in a partial or complete loss of ADH activity.

In some embodiments, the partial or complete loss of activity is in ADH activity capable of converting crotyl alcohol to crotonaldehyde and/or butyraldehyde to butanol. The partial or complete loss of ADH activity allows the microorganism to grow on higher crotyl alcohol levels as well as in some embodiments grow at a faster rate on crotyl alcohol compared to the parental host microorganism or a microorganism without the genetic modification. In other embodiments, the genetic modifications (e.g. deletions) to the adh genes allow the microorganism to accumulate higher crotyl alcohol levels.

Methods for introducing the exogenous gene are described more fully below in reference to crotyl alcohol pathways and other pathways.

Alkene Reductase Activity

In some embodiments, genetic modifications (e.g. deletions) to alkene reductase can cause partial or complete loss of alkene reductase activity. The disclosed alkene reductase enzymes can also use reduced nicotinamide adenine dinucleotide (NADH) and/or NADPH as an electron donor.

In some embodiments, increase in the amount of crotyl alcohol or tolerance to crotyl alcohol can be caused by the disruption of the disclosed alkene reductase which otherwise catalyzes the conversion of crotonaldehyde to butyraldehyde. Deletion in the alkene reductase gene results in reduction or partial or full loss of alkene reductase activity and as shown in FIG. 3 as enzyme G, driving the process towards crotyl alcohol. This in turn eliminates crotyl alcohol from entering other pathways such as into butanol via crotonaldehyde and as shown for example in FIG. 3. In some embodiments, the alkene reductase enzymes deleted are native or endogenous to the engineered microorganism. The native activities may be identified as undesirable activities when they compete with desirable enzyme activities that include crotyl alcohol or crotyl alcohol-derived bioproducts.

Also contemplated here are deletion/disruption of alkene reductase enzyme—encoding genes that include 2-ene-al reductase or α, β-ene-al reductase activity, or enzymes that accept a wide range of α,β-unsaturated alkenals. In other embodiments, the alkene reductase activity may also be reduced/eliminated by deletion of genes that encode those enzymes that have N-ethylmaleimide reductase activity. It was surprisingly found that the nemA gene product was active on 2-ene-als such as crotonaldehyde.

In some embodiments, the alkene reductase activity can also be reduced/eliminated by deletion of genes that encode enzymes from the *E. coli* K12 subgroup. In still other embodiments, the alkene reductase is from *E. coli* str. K12 substr. MG1655 or *E. coli* ATCC 8739 variant. In still other embodiments, the alkene reductase activity is enzyme of sequence of GI: 732684441, SEQ ID NO: 15 of Table 5. In still other embodiments, alkene reductase activity targeted for gene deletion or disruption is encoded by SEQ ID. NO. 5 as shown in Table 5. In some embodiments, the disclosed alkene reductase activity targeted for reduced/elimination of activity may be encoded by the nemA gene from *E. coli*. In some embodiments, the native or endogenous gene that can convert crotonaldehyde to butyraldehyde is deleted in a microorganism.

Other embodiments include alkene reductase activity encoded by the ygjM gene from *B. subtillis*, NADH-dependent flavin oxidoreductase, or it homologs or paralogs in other species, that may be targeted for gene disruption or deletion. Other bacterial homologs include PETN (pentaerythritol tetranitrate) reductase (French C. E., Nicklin S., Bruce N. C. Sequence and properties of pentaerythritol tetranitrate reductase from *Enterobacter cloacae* PB2, J. Bacteriol. 178:6623-6627, 1996), GTN (glycerol trinitrate) reductase (Snape et al., Purification, properties, and sequence of glycerol trinitrate reductase from *Agrobacterium radiobacter*. J. Bacteriol. 179:7796-7802, 1997), MR (morphinone reductase) (French et al., Bacterial morphinone reductase is related to Old Yellow Enzyme. Biochem. J. 312:671-678, 1995), 2-cyclohexenone reductase (Rohde et al., Thermoregulated expression and characterization of an NAD(P)H-dependent 2-cyclohexen-1-one reductase in the plant pathogenic bacterium *Pseudomonas syringae* pv. glycinea. J. Bacteriol. 181:814-822, 1999), and the xenobiotic reductases A and B from *Pseudomonas* sp. (Blehert et al. Cloning and sequence analysis of two *Pseudomonas* flavoprotein xenobiotic reductases. J. Bacteriol. 181:6254-6263, 1999).

Additional alkene reductase enzymes that can be targeted for gene disruption or deletion can be identified based on sequence homologies to the disclosed nemA, ygjM and other sequences described here. In some embodiments, the alkene reductase having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity to the polypeptide or polynucleotide sequence of full length protein sequences of nemA, ygjM or the other alkene reductase enzymes described here.

Accordingly, in some embodiments, the microorganisms may include deletions or disruptions in the ΔnemA gene or ΔygiM gene or homologs thereof and combinations thereof (e.g. ΔnemAΔygjM). In other embodiments, the ygjM gene may be from *Bacillus subtilis*. In other embodiments, the nemA gene from *E. coli* may be deleted. In still other embodiments, the homologs or paralogs of the yjgM gene in *E. coli* may be deleted; the homologs or paralogs of the nemA gene may be deleted from *Bacillus subtilis* or other species.

Such genetic deletions to the disclosed nemA and/or ygjM genes, polynucleotides and/or polypeptides result in a partial or complete loss of alkene reductase activity. The partial or complete loss of alkene reductase activity that results in crotonaldehyde to butyraldehyde allows the microorganism to grow on higher crotyl alcohol levels as well as in some embodiments grow at a faster rate on crotyl alcohol compared to the parental host microorganism or a microorganism without the genetic modification. In other embodiments, the genetic modifications (e.g. deletions) to the alkene reductase genes or activity allow the microorganism to accumulate higher crotyl alcohol levels.

Alkene reductase may also be reduced/eliminated in microorganism of the genus *Acetobacterium*, *Achromobacter*, *Acremonium*, *Agrobacterium*, *Alcaligenes*, *Bacillus*, *Bradyrhizobium*, *Burkholderia*, *Caloramator*, *Castellaniella*, *Cephalosporium*, *Clostridium*, *Escherichia*, *Eubacterium*, *Filifactor*, *Fusobacterium*, *Kluyveromyces*, *Mesorhizobium*, *Moorella*, *Ochrobactrum*, *Oxalophagus*, *Oxobacter*, *Paenibacillus*, *Pseudomonas*, *Ralstonia*, *Rhizobium*, *Rhodotorula*, *Salmonella*, *Shigella*, *Sinorhizobium*, *Sporohalobacter*, *Syntrophospora*, *Thauera*, *Thermoanaerobacter*, *Thermoanaerobacterium*, *Tilachlidium*, *Vibrio*, *Xanthobacter*, or *Yersinia*.

Other, enzymes having α,β-enoate reductase activity include an enzyme from *Acremonium strictum* CBS114157 (deposit date Dec. 19, 2003; deposited under the terms of the Budapest treaty), *Clostridium tyrobutyricum* DSM1460 (available from the Deutsche Sammlung Mikroorganismen und Zellkulturen), *Moorella thermoacetica* DSM1974 (available from the Deutsche Sammlung Mikroorganismen und Zellkulturen) (an enzyme which—also under DSM1974—until Jan. 1, 1980, was named *Clostridium thermoaceticum*), *Ochrobactrum anthropi* NCIMB41200 (deposit date Dec. 16, 2003; deposited under the terms of the Budapest treaty), or *Clostridium kluyveri* DSM555 (available from the Deutsche Sammlung Mikroorganismen und Zellkulturen).

In some embodiments, the alkene reductase and the ADH genes are deleted. In some embodiments, the ADH genes adhE, adhP, yqhD, yahK, or various combinations thereof along with nemA are deleted. For example, the engineered microorganism may have genetic deletions in nemA and in a single gene selected from adhE, adhP, yqhD and yahK or multiple genes selected from (adhE,adhP), (adhE, adhP), or (adhE,yqhD), (adhE,yahK), (adhE,adhP,yqhD), (adhE,adhP, yahK), and (adhE,adhP,yqhD,yahK).

In still other embodiments, the ADH genes adhE, adhP, yqhD, yahK, or various combinations thereof along with ygjM are deleted. For example, the engineered microorganism may have genetic deletions in ygjM and in a single gene selected from adhE, adhP, yqhD and yahK or multiple genes selected from (adhE,adhP), (adhE, adhP), or (adhE,yqhD), (adhE,yahK), (adhE,adhP,yqhD), (adhE,adhP,yahK), and (adhE,adhP,yqhD,yahK).

In still other embodiments, the ADH genes adhE, adhP, yqhD, yahK, or various combinations thereof along with nemA are deleted in *E. coli*. In still other embodiments, the ADH genes and homologs or paralogs of adhE, adhP, yqhD, yahK, or various combinations thereof along with ygjM are deleted in *Bacillus subtilis*.

The disclosed genetic modifications that include gene disruptions or gene deletions that encode for ADH and/or alkene reductase enzymes include a deletion of the entire gene, deletion of portions of the gene, deletion or other modification of a regulatory sequence required for transcription or translation, deletion of a portion of the gene which results in a truncated gene product (e.g., enzyme) or by any of various mutation strategies that reduces activity (including to no detectable activity level) of the encoded gene product. A disruption may broadly include a deletion of all or part of the nucleic acid sequence encoding the enzyme, and also includes, but is not limited to other types of genetic modifications, e.g., introduction of stop codons, frame shift mutations, introduction or removal of portions of the gene, introduction of conditional sensitive mutations (e.g. temperature sensitive), and introduction of a degradation signal, those genetic modifications affecting mRNA transcription levels and/or stability, altering the promoter or repressor upstream of the gene encoding the enzyme and altering mRNA translation, e.g. insertion of stem loop or removing or inactivating an RBS.

In various embodiments, genetic modifications can be to the DNA, mRNA encoded from the DNA, and the corresponding amino acid sequence that results in partial or complete loss of the polypeptide activity. Many different methods can be used to make a cell having partial, reduced or complete loss of the polypeptide activity. For example, a cell can be engineered to have a disrupted regulatory sequence or polypeptide-encoding sequence using common mutagenesis or knock-out technology. See, e.g., Datsenko and Wanner, Proc. Natl. Acad. Sci USA (2000), 97(12): 6640-6645, and Methods in Yeast Genetics (1997 edition), Adams et al., Cold Spring Harbor Press (1998), and Manual of Industrial Microbiology and Biotechnology ($3^{rd}$ edition), edited by Richard H. Baltz, Arnold L. Demain, Julian E. Davies.

One particularly useful method of gene disruption is complete gene deletion because it reduces or eliminates the occurrence of genetic reversions in the genetically modified microorganisms. Accordingly, a disruption of a gene whose product is an enzyme thereby disrupts enzymatic function. Alternatively, antisense technology can be used to reduce the activity of a particular polypeptide. For example, a cell can be engineered to contain a cDNA that encodes an antisense molecule that prevents a polypeptide from being translated. Gene silencing can also be used to reduce the activity of a particular polypeptide (see for example, *Metabolic Engineering of Escherichia Coli Using Synthetic Small Regulatory RNAs*. Na D, Yoo S M, Chung H, Park H, Park J H, Lee S Y; Nature Biotechnology. 2013 February 31(2):170-4).

Thus, in some embodiments, the partial reduction of activity is decreased functional activity. The functional activity can be decreased during either or both the growth or stationary phases. As discussed reduced activity can be achieved for example by deleting a gene, decreasing gene expression, or decreasing the activity or availability of the polypeptide encoded by the gene. The gene can be modified directly, e.g. use of a weaker promoter, one or more amino acid substitutions or deletions or insertions, or can be modulated by modifying its regulatory gene for example.

The resultant genetic disruption or deletion can result in the partial, reduced or complete loss of enzymatic activity. In some embodiments, the enzymatic conversion of the indicated substrate(s) to indicated product(s) under known standard conditions for that enzyme is at least 10, at least 20, at least 30, at least 40, at least 50, at least 60, at least 70, at least 80, or at least 90 percent less than the enzymatic activity for the same biochemical conversion by a native (non-modified) or parental host enzyme under a standard specified conditions.

A cell having reduced enzymatic activity can be identified using any method known in the art. For example, enzyme activity assays can be used to identify cells having reduced enzyme activity, see, for example, Enzyme Nomenclature, Academic Press, Inc., New York 2007. Other assays that may be used to determine the reduction in ADH and alkene reductase include GC/MS analysis. In other examples, levels of NADH/NADPH may be spectroscopically monitored. For example the NADH/NADPH may be monitored colorimetrically using NADP/NADPH assay kits (ab65349) available from ABCAM™.

Gene deletions may be accomplished by mutational gene deletion approaches, and/or starting with a strain having reduced or no expression of one or more of these enzymes, and/or other methods known to those skilled in the art. Gene deletions may be effectuated by any of a number of known specific methodologies, including but not limited to the Red/ET methods.

The Red/ET recombination is known to those of ordinary skill in the art and described in Datsenko and Wanner, Proc. Natl. Acad. Sci USA (2000), 97(12): 6640-6645. Other deletion methods include those described in U.S. Pat. Nos. 6,355,412 and 6,509,156, issued to Stewart et al. Each of these references is incorporated by reference here for its teachings of this method. Material and kits for such method are available from Gene Bridges™ and the method may proceed by following the manufacturer's instructions. The method involves replacement of a target gene by a selectable marker via homologous recombination performed by the recombinase from λ-phage. The host organism expressing λ-red recombinase is transformed with a linear DNA product coding for a selectable marker flanked by the terminal regions (generally ~50 bp, and alternatively up to about ~300 bp) homologous with the target gene. The marker could then be removed by another recombination step performed by a plasmid vector carrying the FLP-recombinase, or another recombinase, such as Cre.

Targeted deletion of parts of microbial chromosomal DNA or the addition of foreign genetic material to microbial chromosomes may be practiced to alter a host cell's metabolism so as to reduce or eliminate production of undesired metabolic products. This may be used in combination with other genetic modifications.

The microorganism can be further genetically modified to increase activity of an enzyme converting crotonaldehyde to crotyl alcohol (see for example, E in FIG. 1 and B in FIG. 3). In some embodiments, the enzyme is a crotonaldehyde reductase (alcohol forming). Increase of a crotonaldehyde reductase (alcohol forming) is used particularly where crotonaldehyde is a by-product and not a bioproduct pathway intermediate.

In some embodiments, some microorganisms include at least one exogenous nucleic acid encoding an enzyme that converts crotonaldehyde to crotyl alcohol. In some embodiments, some microorganisms include at least one exogenous nucleic acid encoding crotonaldehyde reductase (alcohol forming) introduced into the microorganism. In other embodiments, the exogenous nucleic acids that may be increased include those sequences disclosed as SEQ ID NOs: 1-4 and 11-14. In other embodiments, an engineered microorganism with a deletion in the disclosed adh and/or alkene reductase genes may also include at least one exogenous nucleic acid with ADH activity that can convert an aldehyde to an alcohol. In some embodiments, the microorganism includes at least one exogenous nucleic acid of SEQ ID NO: 12 and 14. In other embodiments, the microorganism expresses the gene yqhD and/or yahK.

Enzymes exhibiting crotonaldehyde reductase (alcohol forming) activity are capable of forming crotyl alcohol from crotonaldehyde. The following enzymes can naturally possess this activity or can be engineered to exhibit this activity. Exemplary genes encoding enzymes that catalyze the conversion of an aldehyde to alcohol (e.g., alcohol dehydrogenase or equivalently aldehyde reductase) include genes encoding a medium-chain alcohol dehydrogenase for C2-C14 (Tani et al, Appl. Environ. Microbiol. 66:5231-5235 (2000)), ADH2 from *Saccharomyces cerevisiae* (Atsumi et al, Nature 451:86-89 (2008)), yqhD from *E. coli* which has preference for molecules longer than C(3) (Sulzenbacher et al., J. Mol. Biol. 342:489-502 (2004)), and bdh I and bdh II from *C. acetobutylicum* which converts butyraldehyde into butanol (Walter et al, J. Bacteriol. 174:7149-7158 (1992)). ADH1 from *Zymomonas mobilis* has been demonstrated to have activity on a number of aldehydes including formaldehyde, acetaldehyde, propionaldehyde, butyraldehyde, and acrolein (Kinoshita, Appl. Microbiol. Biotechnol. 22:249-254 (1985)). Cbei_2181 from *Clostridium beijerinckii* NCIMB 8052 encodes yet another useful alcohol dehydrogenase capable of converting crotonaldehyde to crotyl alcohol.

TABLE 3

| Protein | GenBank ID | GI Number | Organism |
| --- | --- | --- | --- |
| alrA | BAB12273.1 | 9967138 | *Acinetobacter* sp. Strain M-1 |
| ADH2 | NP_014032.1 | 6323961 | *Saccharomyces cerevisiae* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |
| Cbei_2181 | YP_001309304.1 | 150017050 | *Clostridium beijerinckii* NCIMB 8052 |

Enzymes exhibiting 4-hydroxybutyrate dehydrogenase activity (EC 1.1.1.61) also fall into this category. Such enzymes have been characterized in *Ralstonia eutropha* (Bravo et al., J. Forensic Sci. 49:379-387 (2004)), *Clostridium kluyveri* (Wolff et al., Protein Expr. Purif. 6:206-212 (1995)) and *Arabidopsis thaliana* (Breitkreuz et al, J. Biol. Chem. 278:41552-41556 (2003)).

TABLE 4

| Protein | GenBank ID | GI Number | Organism |
| --- | --- | --- | --- |
| 4hbd | YP_726053.1 | 113867564 | *Ralstonia eutropha* H16 |
| 4hbd | L21902.1 | 146348486 | *Clostridium kluyveri* DSM 555 |
| 4hbd | Q94B07 | 75249805 | *Arabidopsis thaliana* |

Crotyl Alcohol Pathways

The disclosed engineered microorganisms with the gene deletions or disruptions that cause the partial or full loss of ADH and/or alkene reductase activity may be used in the production of crotyl alcohol or other bioproducts that are produced using crotyl alcohol as an intermediate. Such disclosed engineered microorganisms may also include crotyl alcohol pathways. Numerous microorganisms and enzymatic pathways to produce crotyl alcohol or use crotyl alcohol as an intermediate to a bioproduct are known. For example, with reference to FIG. 1, the engineered microorganisms can have one of the following pathways: EF; ABCDE; ABCK; ABCIJE; LK, MK, NK, OK; LDE; MDE; NDE, ODE; LIJE, MIJE; NIJE; OIJE and each combination of any one or more of A, B, C, D, E, F, I, J, K, L, M, N and O. Details for the pathways to crotyl alcohol or for conversion of crotyl alcohol to butadiene described in FIG. 1 can be found, for example, in PCT International Application Publication No. WO 2011/140171 titled Microorganisms and Methods for the Biosynthesis of Butadiene. In some embodiments, the engineered microorganism with a deletion in ADH, alkene reductase or both may include any one of more of the steps and enzymes shown in FIG. 1. Other exemplary pathways for crotyl production include those described in PCT International Application Publication No. WO 2011/140171 titled Microorganisms and Methods for the Biosynthesis of Butadiene and in PCT International Application Publication No WO 2014/152434 titled Microorganisms and Methods for Producing Butadiene and Related Compounds by Formate Assimilation. Other exemplary pathways for crotyl alcohol production include U.S. Application No. 62/020,901 filed Jul. 3, 2014 and U.S. Application No. 62/082,747 filed Nov. 21, 2014, both titled Microorganisms for Producing 4C-5C Compounds with Unsaturation and Methods Related Thereto. Still other exemplary pathways to crotyl alcohol or for conversion of crotyl alcohol to butadiene include PCT International Application Publication No. WO 2013/057194 titled Process for the Enzymatic Production of Butadiene from Crotyl Alcohol and PCT International Application Publication No. WO 2013/188546 titled Methods for biosynthesizing 1,3 butadiene.

Each of these cited patents or patent applications are incorporated herein by reference in their entirety.

Depending on the crotyl alcohol biosynthetic pathway constituents of a selected host microbial organism, the engineered microorganism can include at least one exogenously expressed crotyl alcohol pathway-encoding nucleic acid and up to all encoding nucleic acids for one or more crotyl alcohol biosynthetic pathways. For example, crotyl alcohol biosynthesis can be established in a host deficient in a pathway enzyme or protein through exogenous expression of the corresponding encoding nucleic acid. In a host deficient in all enzymes or proteins of a crotyl alcohol pathway, exogenous expression of all enzyme or proteins in the pathway can be included, although it is understood that all enzymes or proteins of a pathway can be expressed even if the host contains at least one of the pathway enzymes or proteins. For example, exogenous expression of all nucleic acids and/or polypeptides encoding enzymes or proteins in a pathway for production crotyl alcohol can be included, such as an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotyl alcohol kinase, (FIG. 1, steps A-E).

Bioproducts Via Crotyl Alcohol

Once the crotyl alcohol is obtained or produced by the disclosed engineered microorganism and methods, the crotyl alcohol can be converted to a desired bioproduct (e.g. butadiene, 1,3-butanediol, methyl vinyl carbinol). For example, the crotyl alcohol can be further used as an intermediate in the bioproduction of 3-Buten-2-ol (also referred to as methyl vinyl carbinol (MVC)) and/or butadiene by biosynthetic processes, chemical or enzymatic processes.

Figure 2:
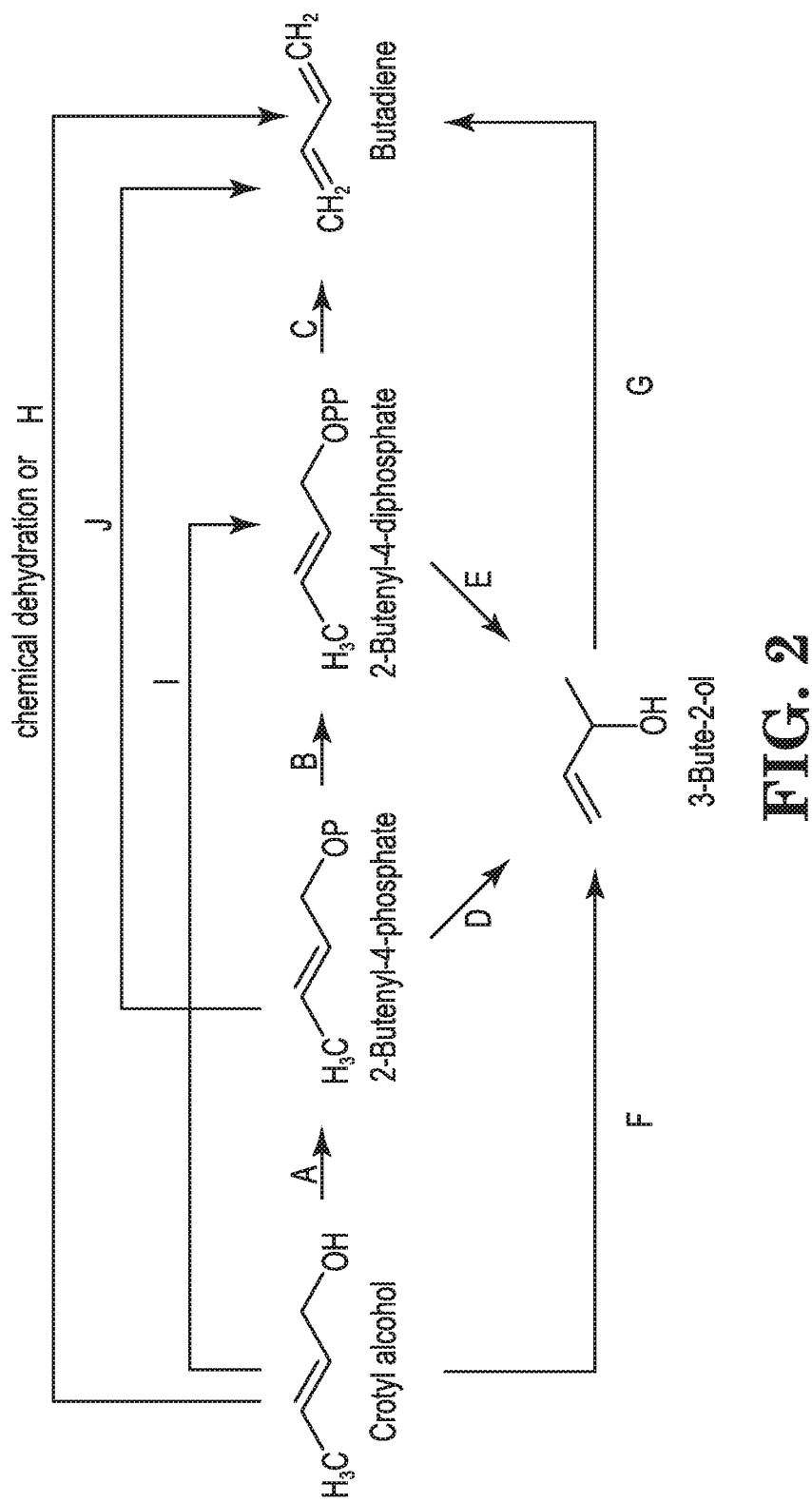
FIG. 2 shows exemplary pathways for converting crotyl alcohol (2-buten-1-ol) to 3-buten-2-ol and/or butadiene. Enzymes are A. crotyl alcohol kinase, B. 2-butenyl-4-phosphate kinase, C. butadiene synthase, D. 3-buten-2-ol synthase, E. 3-buten-2-ol synthase, F. crotyl alcohol isomerase, a vinylisomerase, G. 3-buten-2-ol dehydratase, H. crotyl alcohol dehydratase, a dehydratase/vinylisomerase, I. crotyl alcohol diphosphokinase, J. butadiene synthase (from 2-butenyl-4-phosphate). Crotyl alcohol can be chemically dehydrated to butadiene.

FIG. 1 and FIG. 2 provide exemplary pathways to butadiene from crotyl alcohol. FIG. 2 provides an exemplary pathway to butadiene via one or more of the following intermediates: 2-butenyl-4-phosphate, 2-butenyl-4-diphosphate, and/or 3-buten-2-ol. Optionally, crotyl alcohol can be introduced into this pathway via any crotyl alcohol-producing pathway known in the art, and including conversion from 3-buten-1-ol or 3-buten-2-ol. In some embodiments, the crotyl alcohol is produced by a pathway of FIG. 1 and then introduced into a pathway of FIG. 2.

With reference to FIG. 2, the engineered microbial organism can have any one of the following pathways: D; DG;

AD; ADG; E; EG; BE; BEG; ABE; ABEG; IE; IEG; F; FG; G; H; J; AJ; A; AB; ABC and each combination of any one or more of steps D, E, F with any one or more of steps of FIG. 2, where when at least one of A, B, C, G or H is present then (i) at least one other novel step or pathway is present. Further details for the pathways described in FIG. 2 are found, for example, in PCT International Application Publication No. WO 2011/140171, in PCT International Application Publication No WO 2014/152434 titled Microorganisms and Methods for Producing Butadiene and Related Compounds by Formate Assimilation, and in PCT International Application Publication No. WO 2014/033129 titled Production of volatile dienes by enzymatic dehydration of light alkenols, U.S. Application No. 62/020,901 filed Jul. 3, 2014 and U.S. Application No. 62/082,747 filed Nov. 21, 2014, both titled Microorganisms for Producing 4C-5C Compounds with Unsaturation and Methods Related Thereto and in other references described herein. For example, enzymes suitable for FIG. 2 Steps F, G or H can be in the EC 4.2.1 class, of which linalool dehydratase assigned to EC 4.2.1.127 or a variant thereof is of particular interest. Variants of linalool dehydratase have been reported in PCT International Application Publication No. WO 2014/184345. Still other microorganisms and pathways can be found in PCT International Application Publication No. WO 2013/188546 titled Methods for biosynthesizing 1,3 butadiene. Thus a parental cell provided herein includes a microorganism comprising a pathway to crotyl alcohol as shown in FIG. 1 and a dehydratase such as a linalool dehydratase.

Other exemplary pathways for the production of butadiene include those described in PCT International Application Publication No. WO 2011/140171 titled Microorganisms and Methods for the Biosynthesis of Butadiene; and U.S. Application No. 62/020,901 filed Jul. 3, 2014 and U.S. Application No. 62/082,747 filed Nov. 21, 2014, both titled Microorganisms for Producing 4C-5C Compounds with Unsaturation and Methods Related Thereto.

Sources of encoding nucleic acids for a butadiene, crotyl alcohol, 3-buten-2-ol, pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human.

Exemplary species for such sources include, for example, *Escherichia* species, including *Escherichia coli, Escherichia fergusonii, Castellaniella defragrans, Thauera linaloolentis, Thauera terpenica, Methanocaldococcus jannaschii, Leptospira interrrogans, Geobacter sulfurreducens, Chloroflexus aurantiacus, Roseiflexus* sp. RS-1, *Chloroflexus aggregans, Achromobacter xylosoxydans, Clostrdia* species, including *Clostridium kluyveri, Clostridium symbiosum, Clostridium acetobutylicum, Clostridium saccharoperbutylacetonicum, Clostridium ljungdahlii, Trichomonas vaginalis* G3, *Trypanosoma brucei, Acidaminococcus fermentans, Fusobacterium* species, including *Fusobacterium nucleatum, Fusobacterium mortiferum, Corynebacterium glutamicum, Rattus norvegicus, Homo sapiens, Saccharomyces* species, including *Saccharomyces cerevisiae, Apsergillus* species, including *Aspergillus terreus, Aspergillus oryzae, Aspergillus niger, Gibberella zeae, Pichia stipitis, Mycobacterium* species, including *Mycobacterium smegmatis, Mycobacterium avium*, including subsp. *pratuberculosis, Salinispora arenicola Pseudomonas* species, including *Pseudomonas* sp. CF600, *Pseudomonas putida, Pseudomonas fluorescens, Pseudomonas aeruginosa, Ralstonia* species, including *Ralstonia eutropha, Ralstonia eutropha* JMP134, *Ralstonia eutropha* H16, *Ralstonia pickettii, Lactobacillus plantarum, Klebsiella oxytoca, Bacillus* species, including *Bacillus subtilis, Bacillus pumilus, Bacillus megaterium, Pedicoccus pentosaceus, Chlorofexus* species, including *Chloroflexus aurantiacus, Chloroflexus aggregans, Rhodobacter sphaeroides, Methanocaldococcus jannaschii, Leptospira interrrogans, Candida maltosa, Salmonella* species, including *Salmonella enterica serovar Typhimurium, Shewanella* species, including *Shewanella oneidensis, Shewanella* sp. MR-4, *Alcaligenes faecalis, Geobacillus stearothermophilus, Serratia marcescens, Vibrio cholerae, Eubacterium barkeri, Bacteroides capillosus, Archaeoglobus fulgidus, Archaeoglobus fulgidus, Haloarcula marismortui, Pyrobaculum aerophilum* str. IM2, *Rhizobium* species, including *Rhizobium leguminosarum*, as well as other exemplary species disclosed here or available as source organisms for corresponding genes.

However, with the complete genome sequence available for now more than 550 species (with more than half of these available on public databases such as the NCBI), including 395 microorganism genomes and a variety of yeast, fungi, plant, and mammalian genomes, the identification of genes encoding the requisite butadiene, crotyl alcohol, 3-buten-2-ol, biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of butadiene, crotyl alcohol, 3-buten-2-ol described here with reference to a particular organism such as *E. coli* can be readily applied to other microorganisms, including prokaryotic and eukaryotic organisms alike. Given the teachings and guidance provided here, those skilled in the art will know that a metabolic alteration exemplified in one organism can be applied equally to other organisms.

In addition to direct fermentation to produce butadiene, crotyl alcohol or 3-buten-2-ol (methyl vinyl carbinol) can be separated, purified (for any use), and then dehydrated to butadiene in a second step involving metal-based catalysis, see for example FIG. 2. Suitable product pathways and enzymes, methods for screening and methods for isolating are found in: WO2011140171A2 published 10 Nov. 2011 entitled Microorganisms and Methods for the Biosynthesis of Butadiene; WO2012018624A2 published 9 Feb. 2012 entitled Microorganisms and Methods for the Biosynthesis of Aromatics, 2, 4-Pentadienoate and 1, 3-Butadiene; O2011140171A2 published 10 Nov. 2011 entitled Microorganisms and Methods for the Biosynthesis of Butadiene; WO2013040383A1 published 21 Mar. 2013 entitled Microorganisms and Methods for Producing Alkenes; WO2012177710A1 published 27 Dec. 2012 entitled Microorganisms for Producing Butadiene and Methods Related thereto; WO2012106516A1 published 9 Aug. 2012 entitled Microorganisms and Methods for the Biosynthesis of Butadiene; WO2013028519A1 published 28 Feb. 2013 entitled Microorganisms and Methods for Producing 2,4-Pentadienoate, Butadiene, Propylene, 1,3-Butanediol and Related Alcohols; and U.S. Ser. No. 61/799,255 filed 15 Mar. 2013.

The chemical process includes dehydration to butadiene. Alcohol dehydration is known in the art and can include various thermal processes, both catalyzed and non-catalyzed. In some embodiments, a catalyzed thermal dehydration employs a metal oxide catalyst or silica. In some embodiments, the process is performed by chemical dehydration in the presence of a catalyst. For example, it has been indicated that crotyl alcohol can be dehydrated over bismuth molybdate (Adams, C. R. J. Catal. 10:355-361, 1968) to afford 1,3-butadiene (e.g. see FIG. 2).

Dehydration can be achieved via activation of the alcohol group and subsequent elimination by standard elimination mechanisms such as E1 or E2 elimination. Activation can be achieved by way of conversion of the alcohol group to a halogen such as iodide, chloride, or bromide.

Activation can also be accomplished by way of a sulfonyl, phosphate or other activating functionality that convert the alcohol into a good leaving group. In some embodiments, the activating group is a sulfate or sulfate ester selected from a tosylate, a mesylate, a nosylate, a brosylate, and a triflate. In some embodiments, the leaving group is a phosphate or phosphate ester. In some such embodiments, the dehydrating agent is phosphorus pentoxide.

In a typical process for converting crotyl alcohol into butadiene, crotyl alcohol is passed, either neat or in a solvent, and either in presence or absence of steam, over a solid inorganic, organic or metal-containing dehydration catalyst heated to temperatures in the range of 40-400° C. inside of the reaction vessel or tube, leading to elimination of water and release of butadiene as a gas, which is condensed (butadiene bp=−4.4° C.) and collected in a reservoir for further processing, storage, or use. Typical catalysts can include bismuth molybdate, phosphate-phosphoric acid, cerium oxide, kaolin-iron oxide, kaolin-phosphoric acid, silica-alumina, and alumina. Typical process throughputs are in the range of 0.1-20,000 kg/h. Typical solvents are toluene, heptane, octane, ethylbenzene, and xylene.

In other embodiments, butadiene can be produced by the enzymatic conversion of crotyl alcohol via crotyl phosphate or crotyl diphosphate and as disclosed in WO 2013/057194 or via enzymatic dehydration (isomerization/dehydration) by an enzyme of the EC 4.2.1 class, preferably a linalool dehydratase, for example as reported in PCT International Application Publication Nos. WO 2014/033129 or WO 2014/184345.

Embodiments are described here with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated here, those skilled in the art will understand that reference to a reaction also constitutes reference to the reactants and products of the reaction. Similarly, unless otherwise expressly stated here, reference to a reactant or product also references the reaction, and reference to any of these metabolic constituents also references the gene or genes encoding the enzymes that catalyze or proteins involved in the referenced reaction, reactant or product. Likewise, given the well-known fields of metabolic biochemistry, enzymology and genomics, reference here to a gene or encoding nucleic acid also constitutes a reference to the corresponding encoded enzyme and the reaction it catalyzes or a protein associated with the reaction as well as the reactants and products of the reaction.

It is understood that when more than one exogenous nucleic acid is included in a microbial organism that the more than one exogenous nucleic acids refer to the referenced encoding nucleic acid or biosynthetic activity, as discussed above. It is further understood, as disclosed here, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed here a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

The engineered microbial organisms can contain stable genetic alterations, which refers to microorganisms that can be cultured for greater than five generations without loss of the genetic alteration. Generally, stable genetic alterations include modifications that persist greater than 10 generations, persist more than about 25 generations, and greater than 50 generations, including indefinitely.

Those skilled in the art will understand that the genetic alterations, including metabolic modifications exemplified here, are described with reference to a suitable host organism such as E. coli and their corresponding metabolic reactions or a suitable source organism for desired genetic material such as genes for a desired metabolic pathway. However, given the complete genome sequencing of a wide variety of organisms and the high level of skill in the area of genomics and molecular biology, those skilled in the art will readily be able to apply the teachings and guidance provided here to essentially all other organisms. For example, the E. coli metabolic alterations exemplified here can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less than 25% can also be considered to have arisen by vertical descent if their three-dimensional structure also shows similarities.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the engineered microorganism. An example of orthologs exhibiting separable activities is where distinct activities have been separated into distinct gene products between two or more species or within a single species.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used here. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the disclosed engineered microbial organisms having biosynthetic capability, those skilled in the art will understand with applying the teaching and guidance provided here to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well-known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.2.29+ (Jan. 6, 2014) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.2.29+ (Jan. 6, 2014) and the following parameters: Match: 1; mismatch: −2; gap open: 5; gap extension: 2; x dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

For various embodiments, the genetic modifications include various genetic manipulations, including those directed to change regulation of, and therefore ultimate activity of, an enzyme or enzymatic activity of an enzyme identified in any of the disclosed pathways. Such genetic modifications may be directed to transcriptional, translational, and post-translational modifications that result in a change of enzyme activity and/or selectivity under selected and/or identified culture conditions and/or to provision of additional nucleic acid sequences such as to increase copy number and/or mutants of an enzyme related to crotyl alcohol production. Specific methodologies and approaches to achieve such genetic modification are well-known to one skilled in the art, and include, but are not limited to increasing expression of an endogenous genetic element; decreasing functionality of a repressor gene; introducing a heterologous genetic element; increasing copy number of a nucleic acid sequence encoding a polypeptide catalyzing an enzymatic conversion step to produce crotyl alcohol; mutating a genetic element to provide a mutated protein to increase specific enzymatic activity; over-expressing; under-expressing; over-expressing a chaperone; knocking out a protease; altering or modifying feedback inhibition; providing an enzyme variant having one or more of an impaired binding site for a repressor and/or competitive inhibitor; knocking out a repressor gene; evolution, selection and/or other approaches to improve mRNA stability as well as use of plasmids having an effective copy number and promoters to achieve an effective level of improvement. Random mutagenesis may be practiced to provide genetic modifications that may fall into any of these or other stated approaches. The genetic modifications further broadly fall into additions (including insertions), deletions (such as by a mutation) and substitutions of one or more nucleic acids in a nucleic acid of interest. In various embodiments a genetic modification results in improved enzymatic specific activity and/or turnover number of an enzyme. Without being limited, changes may be measured by one or more of the following: $K_m$; $k_{cat}$; and $K_{cat}/K_m$=catalytic efficiency.

In one embodiment, the engineered microorganisms with partial or complete loss of ADH and/or alkene reductase activity have improved tolerance to crotonaldehyde and/or crotyl alcohol. In some embodiments the engineered microorganisms include genetic modifications causing full or partial loss of ADH and/or alkene reductase activity and genetic modifications that include crotyl alcohol and/or other pathways that use crotyl alcohol as an intermediate. These various embodiments can be assessed by assaying their growth in crotyl alcohol concentrations that are detrimental to growth of the parental strains. Tolerance to crotyl alcohol may vary depending on the crotyl alcohol concentration, growth conditions and the specific engineered strain. For example, as shown in Example 2, a deletion in adh and/or nemA showed improved growth over the parental strain without the modification.

The engineered microorganisms and methods can be described in terms of their growth in media including crotyl alcohol. Growth can optionally be defined in terms of other parameters such as other media components, the temperature and other conditions in which the cells are grown. It is understood that during culturing, media conditions will constantly change as caused by consumption and depletion of media nutrients by the cells, and the increase in the amount bioproducts in the media such as crotyl alcohol. Accordingly, the cell's growth rate may change at certain points during culturing. Growth and growth rate of cells can optionally be described in a certain amount of a media component, or a certain range of a media component.

Culturing includes growing (proliferation phase) or maintaining the microorganism at a stationary phase. Production of crotyl alcohol or its downstream products can occur in either or both phases In some embodiments, growth of the engineered microbial cell is described in terms of its capability of growing in media containing an amount of crotyl alcohol, where its growth is measured relative to a parental strain that does not have genetic modifications to one or more genes that provides tolerance to crotyl alcohol, and/or increases crotyl production. For example, deletions in genes that encode for ADH and/or alkene reductase activity exhibit an increase in the growth rate in media of 1.1 times or greater as compared to the growth rate of a parent host strain or microorganism that does not have the referenced genetic modifications. The increase in the rate of growth can be measured in media containing 0.001 to about 2 wt % of crotyl alcohol. For example, the engineered microorganism can exhibit a growth rate of 1.2, 1.3, 1.4, 1.5, 1.6, 1.7, 1.8, 1.9, 2.0, 2.1, 2.2, 2.3, 2.4, and 2.5 times that of the parent host strain without the genetic modification. In other embodiments, the engineered microorganism can have a grow rate of about 1.1 times to about 3 times, or about 1.2 times to about 2.5 times that of the parent host strain without the genetic modification.

In some embodiments, the engineered microorganism is grown in culture having more than 0.001% (w/v) of crotyl alcohol, or more than 0.01%, 0.1%, 0.5%, 1% or 2% (w/v) of crotyl alcohol.

In some embodiments, the engineered microorganism is grown in culture having more than 0.138 mM of crotyl alcohol, or more than 1.38 mM 13.8 mM, 69 mM, 138 mM or 276 mM of crotyl alcohol.

In one embodiment, suitable ADH and/or alkene reductase enzymes catalyze the reactions optimally at host cell physiological conditions. In another embodiment, suitable ADH and/or aldehyde reductase enzymes for use catalyze reactions optimally from about pH 4 to about pH 9. In another embodiment, suitable ADH and/or alkene reductase enzymes catalyze reactions optimally from about pH 5 to about pH 8. In another embodiment, suitable ADH and/or alkene reductase enzymes for use catalyze reduction reactions optimally from about pH 6 to about pH 7. In another embodiment, suitable ADH and/or alkene reductase enzymes catalyze reactions optimally from about pH 6.5 to about pH 7. In another embodiment, suitable ADH and/or alkene reductase enzymes for use catalyze reactions optimally at about pH 4, 4.5, 5, 5.5, 6, 6.5, 7, 7.5, 8, 8.5, or 9. In another embodiment, suitable ADH and/or alkene reductase enzymes for use catalyze reactions optimally at about pH 7.

In one embodiment, suitable ADH and/or alkene reductase enzymes for use catalyze reactions optimally at up to about 70° C. In another embodiment, suitable ADH and/or alkene enzymes catalyze reduction reactions optimally at about 10° C., 15° C., 20° C., 25° C., 30° C., 35° C., 40° C., 45° C., 50° C., 55° C., 60° C., 65° C., or 70° C. In another embodiment, suitable ADH and/or alkene reductase enzymes catalyze reactions optimally at about 30° C.

EXAMPLES

Example 1

Strain Construction/Deletion Methods

Alcohol dehydrogenases; adhE (GI: 732684842), yqhD (GI: 16130909), adhP (GI: 732684610), yahK (GI:1657523) and N-ethylmaleimide reductase, nemA (GI: 732684441) were deleted from *E. coli* ATCC 8739 C variant and *E. coli* Str. K-12 substr. MG1655. Strains were constructed using λ red recombination as described in Datsenko and Wanner, Proc Natl Acad Sci USA (2000), 97(12): 6640-6645. Briefly, strains were transformed with pRED plasmid containing arabinose inducible X red recombinase genes and a bla resistance cassette conferring carbenicillin resistance. Transformants carrying the pRED plasmid were then grown in 100 µs/mL carbenicillin and 134 mM arabinose and transformed with linear DNA constructs containing homology arms targeting the gene to be deleted flanking a sacB-kan cassette containing constitutively expressed sacB and kan genes. The kan gene confers kanamycin resistance and allows for selection of cells with integrated sacB-kan cassettes when grown on 50 µg/mL kanamycin. The sacB gene confers sucrose sensitivity and allows a counter selective pressure to select for cells that no longer have the integrated sacB-kan cassette. Cells were grown in the presence of 100 µg/mL carbenicillin and 50 µg/mL kanamycin to confirm integration of sacB-kan cassette and presence of pRed plasmid. Cells were then induced with 134 mM arabinose and transformed with a linear DNA construct replacing the sacB-kan cassette with DNA homologous to chromosomal DNA flanking the desired deletion, effectively deleting the desired DNA sequence (see Table 5 for deleted DNA sequences for each strain). Replacement of the sacB-kan cassette was selected for by growth in 303 mM sucrose.

Chromosomal deletion was confirmed by PCR amplification and sequencing (see Table 5 for primers used for amplification and sequencing).

In this example, for deletion of more than one gene in an organism, the strain with a first deletion was constructed and used for each subsequent gene deletion.

TABLE 5

DNA Sequences deleted from chromosome and primers used and reported in the Sequence Listing.

| Chromosomal Modification | Sequence ID No. |
| --- | --- |
| adhE deletion | SEQ ID NO.: 1 |
| yqhD deletion | SEQ ID NO.: 2 |
| adhP deletion | SEQ ID NO.: 3 |
| yahK deletion | SEQ ID NO.: 4 |
| nemA deletion | SEQ ID NO.: 5 |
| adhEF1 | SEQ ID NO. 6 |
| adhER1 | SEQ ID NO. 7 |
| yqhDF1 | SEQ ID NO. 8 |
| yqhDR1 | SEQ ID NO. 9 |
| adhPF1 | SEQ ID NO. 10 |
| adhPR1 | SEQ ID NO. 11 |
| yahKF1 | SEQ ID NO. 12 |
| yahKR1 | SEQ ID NO. 13 |
| nemAf1 | SEQ ID NO. 14 |
| nemAR1 | SEQ ID NO. 15 |
| adhE protein | SEQ ID NO. 16 |
| yqhD protein | SEQ ID NO. 17 |
| adhP protein | SEQ ID NO. 18 |
| yahK protein | SEQ ID NO. 19 |
| nemA protein | SEQ ID NO. 20 |

Example 2

Crotyl Alcohol Tolerance Studies

E. coli Str. K-12 substr. MG1655 strains 48 (wildtype) and 3-FEDB with multiple deletions (ΔyahkΔadhPΔyqhDΔadhE); and E. coli ATCC 8739 C strains (wildtype) and its variants 3-FISC (ΔadhE), 3-GAEB (ΔadhEΔyqhD), 3-GBOG (ΔadhEΔyqhDΔadhP), and 3-GDOB (ΔadhEΔyqhDΔadhPΔyahK) were struck for single colonies on LB agar from a glycerol freezer stock. Four single colonies per strain were picked and inoculated into 1 mL LB+55.7 mM glucose in deep well 96 well plates and grown at 37° C. overnight (16-20 hours). The optical density of the overnight culture was taken and cells were normalized to $OD_{600}$=1 and spun down. Cells were resuspended in 1 mL of M9 minimal media+11.1 mM glucose. Cells were then spun down and washed again in 1 mL M9+11.1 mM glucose. Bioscreen honeycomb 2 plates (Cat. No. 9502550) were filled with 198 μL M9+11.1 mM glucose or M9+11.1 mM glucose+138 mM crotyl alcohol (Sigma-Aldrich). 2 μL washed cells were added to each well at N=4. Bioscreen honeycomb 2 plates were loaded into a bioscreen C MBR (Oy Growth Curves Ab Ltd) machine, an incubator system set to read turbidity at $OD_{420-580}$ every 15 minutes at 37° C. For growth curve data, see FIG. 4A (E. coli Str. K-12 substr. MG1655 strains) and FIG. 4B (E. coli ATCC 8739 C variant strains).

Figure 4A:
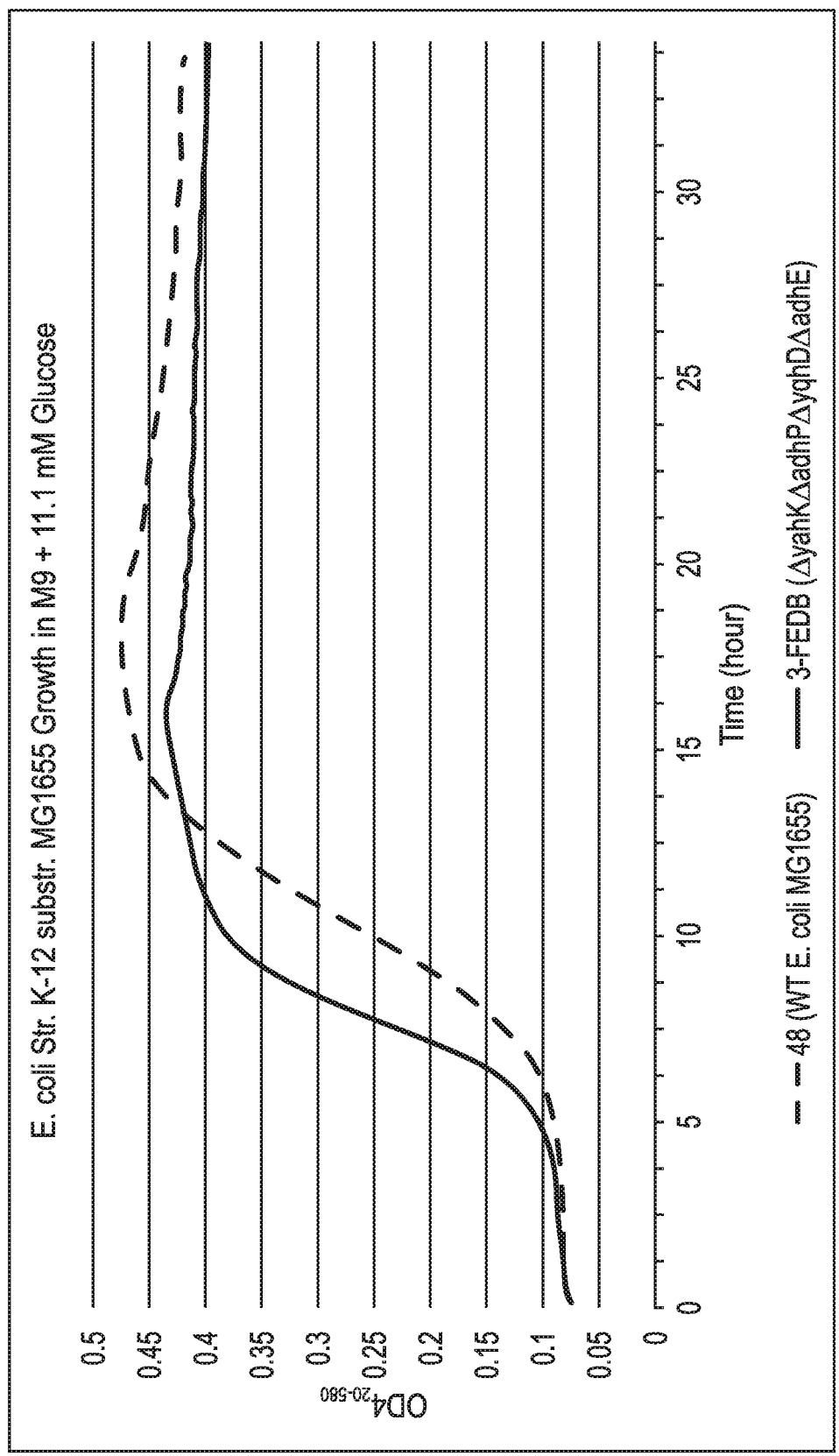
FIGS. 4A-B show growth curves of *E. coli* strain K-12 substr. MG1655 and various modifications grown on glucose (FIG. 4A) and on glucose+crotyl alcohol (FIG. 4B) in terms of culture turbidity at OD420-580 relative to culture time.
Figure 4B:
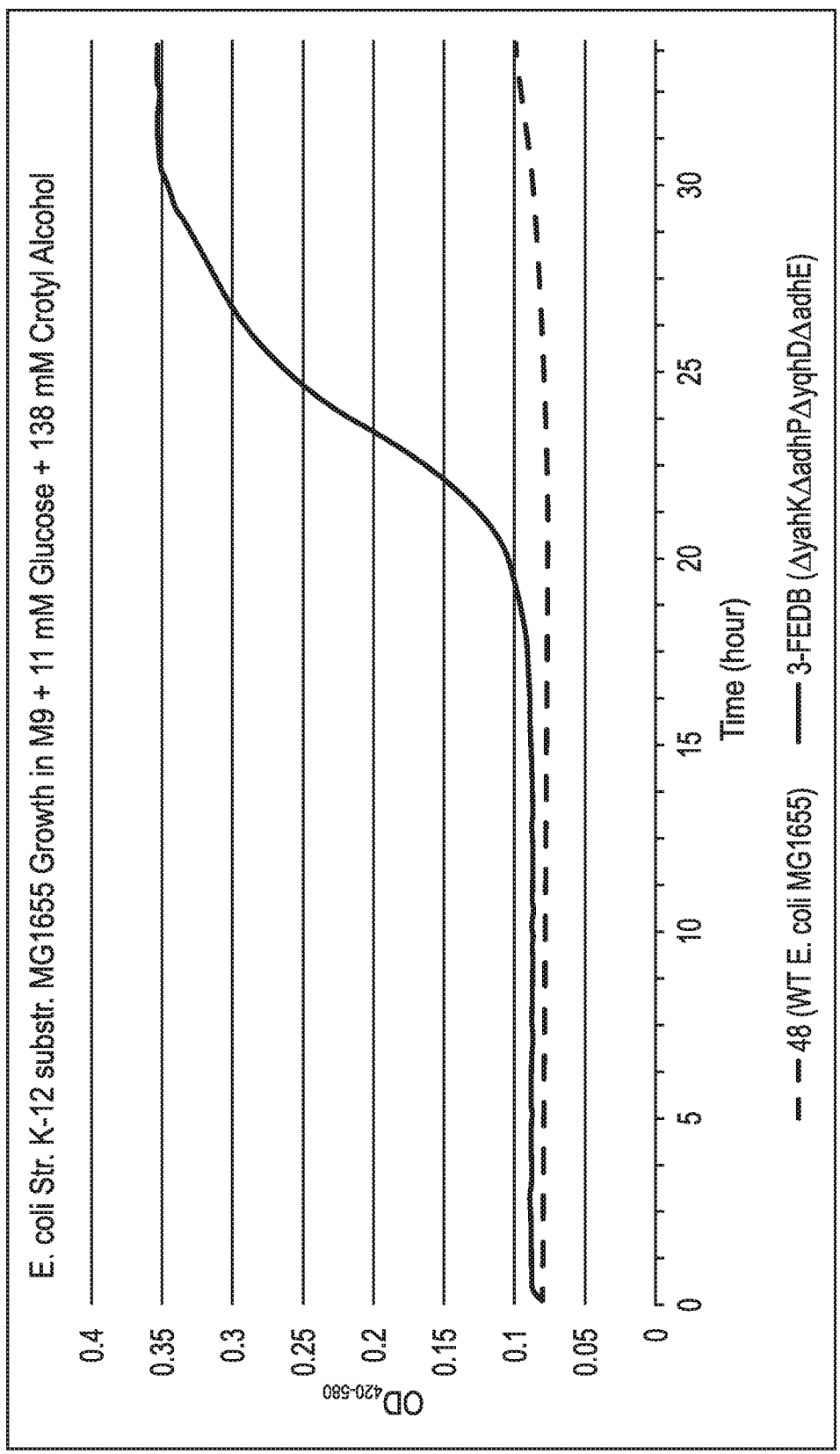

FIG. 4A shows that when grown in the absence of crotyl alcohol, the wild-type or parental strain and the engineered microorganisms show similar growth rates. FIG. 4B shows that when grown in the presence of 138 mM crotyl alcohol, the wild-type or parental strain's growth is inhibited, whereas the engineered microorganism 3-FEDB (ΔyahKΔadhPΔyqhDΔadhE) while showing an initial lag grew on crotyl alcohol.

Figure 5A:
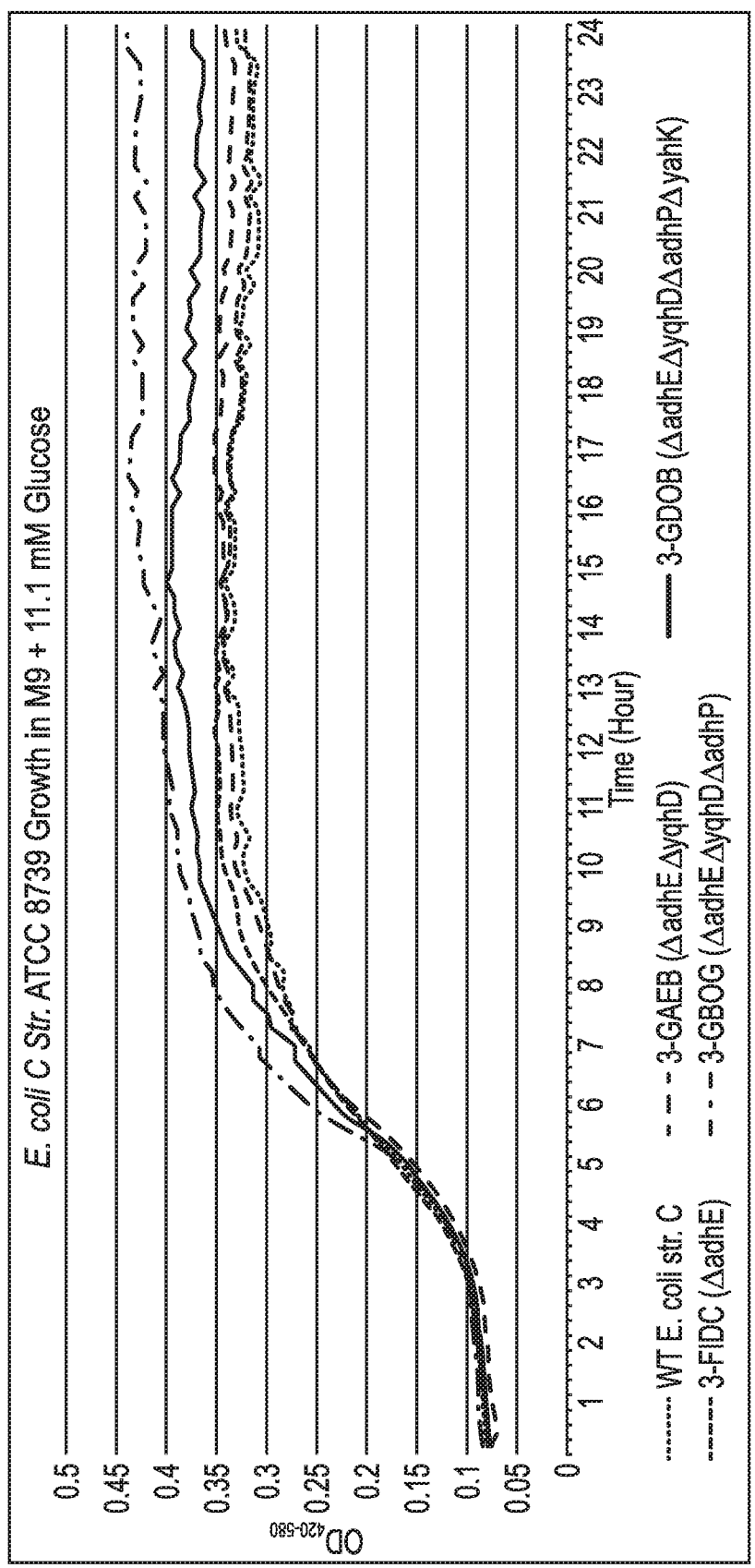
FIGS. 5A-B show growth curves of *E. coli* strains ATCC 8739 and various modifications grown on glucose (FIG. 5A) and grown on glucose+crotyl alcohol (FIG. 5B) in terms of culture turbidity at OD420-580 relative to culture time.
Figure 5B:
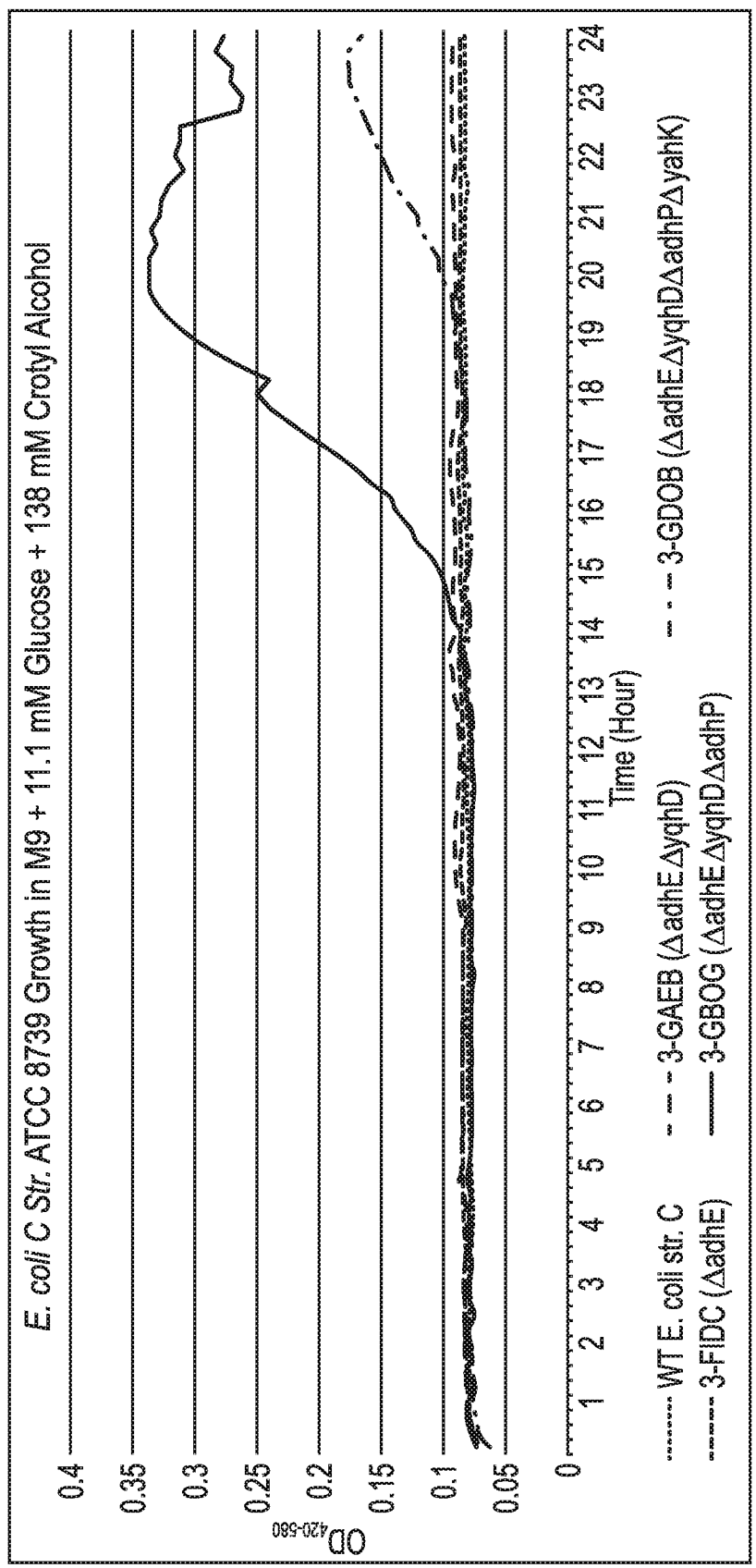

FIG. 5A shows that when grown in the absence of crotyl alcohol, the wild-type or parental strain and the engineered microorganisms show similar, irregular growth rates. FIG. 5B shows that when grown in the presence of 138 mM crotyl alcohol, the wild-type or parental strain's growth is inhibited as are the 3-FIDC (ΔadhE) and 3-GAEB (ΔadhEΔyqhD), whereas the engineered microorganisms 3-GBOG (ΔyahKΔadhPΔyqhDΔadhE) and 3-GBOB (ΔadhEΔyqhDΔadhP) while showing an initial lag grew on crotyl alcohol.

Example 3

NemA Validation Experiments

Strains (ATCC 8739 C variants) 3-GGGF (yqhD+nemA+ parent strain), 3-GHDO (ΔyqhD), 3-HAEF (ΔnemA), and 3-HAEG (ΔyqhDΔnemA) were struck onto LB agar plates from glycerol stock and grown overnight (16-20 hours). Single colonies were picked and inoculated into 30 mL M9+27.8 mM glucose+10 mM crotyl alcohol in baffled flasks and grown overnight (16-20 hours). Overnight cultures were seeded at $OD_{600}$=0.1 into fresh 30 mL M9+55.7 mM glucose+10 mM crotyl alcohol in baffled flasks. 1 mL samples were taken at 4, 8, and 27 hours after growth on crotyl alcohol. Samples were spun down, and the supernatants were submitted for analytical analysis. GCMS analysis of crotyl alcohol and n-butanol in liquid samples by liquid injection. Reduction of butanol was quantified in GCMS chromatograms and line graphs.

GCMS Methods

A GCMS method has been developed monitor the following volatile compounds: n-butanol (n-ButOH) and crotyl alcohol (Crot-OH). This method has good sensitivity with detection limits in low mM range (linearity in 0.5-100 mM). Sensitivity of this assay is compound dependent, being a function of volatility and partial pressures under the conditions used and MS ionization/fragmentation efficiency. Crotyl alcohol and n-butanol standards were purchased from Sigma-Aldrich.

GCMS Analysis

An Agilent gas chromatograph 6890N, interfaced to a mass-selective detector (MSD) 5973, operated in electron impact ionization (EI) mode, was used for the analysis. An INNOWAX column (Agilent—19091N-133), 30 m×0.25 mm i.d.×0.25 μm film thickness, was chosen. Samples were injected by an ALS autosampler operated in direct injection mode. The parameters used were: injection volume 1.0 μL (split ratio 20:1), 250° C. inlet temperature. Helium was used as a carrier gas, and the flow rate maintained at 1.3 mL/min. A temperature program has been optimized to ensure good resolution of the analytes of interest and minimum matrix interference: the oven is initially held at 40° C. for 1 min, then ramped to 41° C. at 1° C./min, second ramp at 35° C./min to 60° C., and final ramp at 100° C./min to 250° C. and hold 4.06 min (total run time 10 min). The data were acquired using low mass. MS tune file settings and 28-150 m/z mass-range scan. Typical retention times (RT) and characteristic mass fragments used for quantitation of the analytes of interest are listed in Table 6. A typical GCMS chromatogram of a standard mix is presented in the figures referred to below. Quantitation was performed based on standard curves using quadratic fit (typically, forced to zero). GCMS data were processed using Agilent MSD Productivity ChemStation software.

TABLE 6

| Analyte | RT, min | Target m/z |
|---|---|---|
| n-propanol (IS) | 4.96 | 59 |
| n-butanol | 5.90 | 56 |
| Trans-crotyl alcohol | 6.29 | 72 |
| Cis-crotyl alcohol | 6.40 | 72 |

The engineered microorganisms 3-GHDO (ΔyqhD), 3-HAEF (ΔnemA), and 3-HAEG with multiple deletions (ΔnemAΔyqhD) exhibited no detectable butanol production whereas they exhibit crotyl alcohol and propanol production, as reported in FIG. 6A-6D based on GC/MS chromatographs of organisms grown on crotyl alcohol-containing media and assayed for n-propanol, butanol and crotyl alcohol for 4, 8 and 27 hours.

What is claimed is:

1. A method for producing a crotyl alcohol using an engineered *Escherichia coli* (*E. coli*) or *Bacillus subtilis* (*B. subtilis*), the method comprising:
culturing the engineered *E. coli* or *B. subtilis* to produce crotyl alcohol, wherein the engineered *E. coli* or *B. subtilis* comprises at least one genetic modification causing partial or complete loss of activity in an alkene reductase encoded by nemA and having at least 90% sequence identity to SEQ ID NO: 5; or an alkene reductase encoded by nemA and having at least 90% sequence identity to SEQ ID NO: 5 and an alcohol dehydrogenase (ADH) having at least 90% sequence identities to SEQ ID NO: 1 (adhE), SEQ ID NO: 2 (yqhD), SEQ ID NO: 3 (adhP), SEQ ID NO: 4 (yahK), or combinations thereof.

2. An engineered *Escherichia coli* (*E. coli*) or *Bacillus subtilis* (*B. subtilis*) comprising at least one genetic modification causing partial or complete loss of activity in an alkene reductase encoded by nemA and having at least 90% sequence identity to SEQ ID NO: 5; or an alkene reductase encoded by nemA and having at least 90% sequence identity to SEQ ID NO: 5 and an alcohol dehydrogenase (ADH) having at least 90% sequence identities to SEQ ID NO: 1 (adhE), SEQ ID NO: 2 (yqhD), SEQ ID NO: 3 (adhP), SEQ ID NO: 4 (yahK), or combinations thereof and at least one exogenous nucleic acid encoding an enzyme of a crotyl alcohol pathway.

3. The engineered microorganism of claim 1, wherein the alcohol dehydrogenase converts crotyl alcohol to crotonaldehyde, or converts butyraldehyde to butanol.

4. The method of claim 1, wherein the engineered *E. coli* has genetic deletions in single genes selected from adhE, adhP, yqhD and yahK or multiple genes selected from (adhE,adhP), (adhE, adhP), or (adhE,yqhD), (adhE,yahK), (adhE,adhP,yqhD), (adhE,adhP,yahK), and (adhE,adhP,yqhD,yahK).

5. The method of claim 1, wherein the partial or complete loss of ADH reduces the accumulation or conversion of crotyl alcohol to crotonaldehyde or butrylaldehyde to butanol, or both.

6. The method of claim 1, wherein the partial or complete loss of alkene reductase reduces the accumulation or conversion of butryaldehyde and/or butanol.

7. The method of claim 1, wherein the engineered *B. subtilis* has a genetic deletion in yqjM gene in *B. subtilis*.

8. The method of claim 1, wherein the engineered *E. coli* has the nemA deletion in *E. coli*.

9. The method of claim 1, wherein the engineered *E. coli* has genetic deletions in nemA and in a single gene selected from adhE, adhP, yqhD and yahK or multiple genes selected from (adhE,adhP), (adhE, adhP), or (adhE,yqhD), (adhE, yahK), (adhE,adhP,yqhD), (adhE,adhP,yahK), and (adhE, adhP,yqhD,yahK).

10. The method of claim 9, wherein the engineered microorganism with the deletions are in *E. coli*.

11. The method of claim 1, wherein the engineered microorganism has genetic deletions in yqjM and in a single gene selected from adhE, adhP, yqhD and yahK or multiple genes selected from (adhE,adhP), (adhE, adhP), or (adhE, yqhD), (adhE,yahK), (adhE,adhP,yqhD), (adhE,adhP,yahK), and (adhE,adhP,yqhD,yahK).

12. The method of claim 1, wherein the crotyl alcohol bioproduct pathway comprises an acetyl-CoA:acetyl-CoA acyltransferase, an acetoacetyl-CoA reductase, a 3-hydroxybutyryl-CoA dehydratase, a crotonyl-CoA reductase (aldehyde forming), a crotonaldehyde reductase (alcohol forming), a crotonyl-CoA hydrolase, synthetase, or transferase, a crotonate reductase, a crotonyl-CoA reductase (alcohol forming), a glutaconyl-CoA decarboxylase, a glutaryl-CoA dehydrogenase, a 3-aminobutyryl-CoA deaminase, or a 4-hydroxybutyryl-CoA dehydratase.

13. The method of claim 1, wherein the microorganism comprises an enzyme converting crotyl alcohol to 1,3-butadiene, or where the enzyme is a linalool dehydratase or variant thereof.

14. The method of claim 1, wherein the crotyl alcohol produced is converted to 3-buten-2-ol and/or butadiene.

15. The of claim 1, wherein the conversion of crotyl alcohol to butadiene is by chemical dehydration in the presence of a catalyst; by enzymatic conversion of crotyl alcohol into butadiene or by growing an engineered microorganism that can convert crotyl alcohol to butadiene.

16. The method of claim 1, wherein the engineered *E. coli* is *Escherichia coli* K-12MG1655 or *Escherichia coli* ATCC 8739 C variant.

17. The method of claim 1, wherein the engineered *E. coli* or *B. subtilis* exhibits an increased growth on crotyl alcohol compared to a parental host microorganism that does not have the genetic modifications.

18. The method of claim 1, wherein the engineered *E. coli* or *B. subtilis* grows on medium containing about 0.138 mM to about 138 mM crotyl alcohol.

19. A cell culture composition comprising crotyl alcohol, methylvinyl carbinol or butadiene produced by the method of claim 1.

20. A method for producing a crotyl alcohol using an engineered *Escherichia coli* (*E. coli*), the method comprising:
culturing an engineered *E. coli* to produce crotyl alcohol, the engineered *E. coli* comprises at least one genetic modification causing partial or complete loss of activity in an alkene reductase that converts crotonaldehyde to butryldehyde where the alkene reductase is encoded by nemA having at least 90% sequence identity to SEQ ID NO: 5.

* * * * *

```
                        SEQUENCE LISTING

<160> NUMBER OF SEQ ID NOS: 20

<210> SEQ ID NO 1
<211> LENGTH: 2065
<212> TYPE: DNA
<213> ORGANISM: Escherichia coli

<400> SEQUENCE: 1
cgctgaacca atcggtatta tttgcggtat cgttccgacc actaacccga cttcaactgc    60
tatcttcaaa tcgctgatca gtctgaagac ccgtaacgcc attatcttct ccccgcaccc   120
gcgtgcaaaa gatgccacca acaaagcggc tgatatcgtt ctgcaggctg ctatcgctgc   180
cggtgctccg aaagatctga tcggctggat cgatcaacct tctgttgaac tgtctaacgc   240
actgatgcac cacccagaca tcaacctgat cctcgcgact ggtggtccgg gcatggttaa   300
agccgcatac agctccggta aaccagctat cggtgtaggc gcgggcaaca ctccagttgt   360
tatcgatgaa actgctgata tcaaacgtgc agttgcatct gtactgatgt ccaaaacctt   420
cgacaacggc gtaatctgtg cttctgaaca gtctgttgtt gttgttgact ctgtttatga   480
cgctgtacgt gaacgttttg caacccacgg cggctatctg ttgcagggta agagctgaa    540 agctgttcag gatgttatcc tgaaaaacg tgcgctgaac gcggctatcg ttggtcagcc   600
agcctataaa attgctgaac tggcaggctt ctctgtacca gaaaacacca gattctgat    660 cggtgaagtg accgttgttg atgaaagcga accgttcgca catgaaaaac tgtccccgac   720
tctggcaatg taccgcgcta agatttcga agacgcggta gaaaagcag agaaactggt    780 tgctatgggc ggtatcggtc atacctcttg cctgtacact gaccaggata accaaccggc   840
tcgcgtttct tacttcggtc agaaaatgaa aacggcgcgt atcctgatta cacccagc     900 gtctcagggt ggtatcggtg acctgtataa cttcaaactc gcaccttccc tgactctggg   960
ttgtggttct tggggtggta actccatctc tgaaaacgtt ggtccgaaac acctgatcaa  1020
caagaaaacc gttgctaagc gagctgaaaa catgttgtgg cacaaacttc cgaaatctat  1080
ctacttccgc cgtggctccc tgccaatcgc gctggatgaa gtgattactg atggccacaa  1140
acgtgcgctc atcgtgactg accgcttcct gttcaacaat ggttatgctg atcagatcac  1200
ttccgtactg aaagcagcag gcgttgaaac tgaagtcttc ttcgaagtag aagcggaccc  1260 gacctgagc atcgttcgta aggtgcaga actggcaaac tccttcaaac cagacgtgat   1320
tatcgcgctg ggtggtggtt ccccgatgga cgccgcgaag atcatgtggg ttatgtacga  1380
acatccggaa actcacttcg aagagctggc gctgcgcttt atggatatcc gtaaacgtat  1440
ctacaagttc ccgaaaatgg cgtgaaagc gaaaatgatc gctgtcacca ccacttctgg  1500
tacaggttct gaagtcactc cgtttgcggt tgtaactgac gacgctactg gtcagaaata  1560
tccgctggca gactatgcgc tgactccgga tatggcgatt gtcgacgcca acctggttat  1620
ggacatgccg aagtccctgt gtgctttcgg tggtctggac gcagtaactc acgccatgga  1680
agcttatgtt tctgtactgg catctgagtt ctctgatggt caggctctgc aggcactgaa  1740
```

```
actgctgaaa gaatatctgc cagcgtccta ccacgaaggg tctaaaaatc cggtagcgcg    1800
tgaacgtgtt cacagtgcag cgactatcgc gggtatcgcg tttgcgaacg ccttcctggg    1860
tgtatgtcac tcaatggcgc acaaactggg ttcccagttc catattccgc acggtctggc    1920
aaacgccctg ctgatttgta acgttattcg ctacaatgcg aacgacaacc cgaccaagca    1980
gactgcattc agccagtatg accgtccgca ggctcgccgt cgttatgctg aaattgccga    2040
ccacttgggt ctgagcgcac cgggc                                           2065

<210> SEQ ID NO 2
<211> LENGTH: 1164
<212> TYPE: DNA
<213> ORGANISM: Escherichia coli

<400> SEQUENCE: 2
atgaacaact ttaatctgca caccccaacc cgcattctgt ttggtaaagg cgcaatcgct      60
ggtttacgcg aacaaattcc tcacgatgct cgcgtattga ttacctacgg cggcggcagc    120
gtgaaaaaaa ccggcgttct cgatcaagtt ctggatgccc tgaaaggcat ggacgtgctg    180
gaatttggcg gtattgagcc aaacccggct tatgaaacgc tgatgaacgc cgtgaaactg    240
gttcgcgaac agaaagtgac tttcctgctg gcggttggcg gcggttctgt actggacggc    300
accaaattta tcgccgcagc ggctaactat ccggaaaata tcgatccgtg gcacattctg    360
caaacgggcg gtaaagagat taaaagcgcc atcccgatgg gctgtgtgct gacgctgcca    420
gcaaccggtt cagaatccaa cgcaggcgcg gtgatctccc gtaaaaccac aggcgacaag    480
caggcgttcc attctgccca tgttcagccg gtatttgccg tgctcgatcc ggtttatacc    540
tacacccctg cgccgcgtca ggtggctaac ggcgtagtgg acgcctttgt acacaccgtg    600
gaacagtatg ttaccaaacc ggttgatgcc aaaattcagg accgtttcgc agaaggcatt    660
ttgctgacgc taatcgaaga tggtccgaaa gccctgaaag agccagaaaa ctacgatgtg    720
cgcgccaacg tcatgtgggc ggcgactcag gcgctgaacg gtttgattgg cgctggcgta    780
ccgcaggact gggcaacgca tatgctgggc acgaactga ctgcgatgca cggtctggat    840
cacgcgcaaa cactggctat cgtcctgcct gcactgtgga atgaaaaacg cgataccaag    900
cgcgctaagc tgctgcaata tgctgaacgc gtctggaaca tcactgaagg ttccgatgat    960
gagcgtattg acgccgcgat tgccgcaacc cgcaatttct ttgagcaatt aggcgtgccg   1020
acccacctct ccgactacgg tctggacggc agctccatcc cggctttgct gaaaaaactg   1080
gaagagcacg gcatgaccca actgggcgaa atcatgaca ttacgttgga tgtcagccgc   1140
cgtatatacg aagccgcccg ctaa                                          1164

<210> SEQ ID NO 3
<211> LENGTH: 1011
<212> TYPE: DNA
<213> ORGANISM: Escherichia coli

<400> SEQUENCE: 3
atgaaggctg cagttgttac gaaggatcat catgttgacg ttacgtataa aacactgcgc      60
tcactgaaac atggcgaagc cctgctgaaa atggagtgtt gtggtgtatg tcataccgat    120
cttcatgtta agaatggcga ttttggtgac aaaaccggcg taattctggg ccatgaaggc    180
atcggtgtgg tggcagaagt gggtccaggt gtcacctcat aaaaccagg cgatcgtgcc    240 agcgtggcgt ggttctacga aggatgcggt cattgcgaat actgtaacag tggtaacgaa    300
```

```
acgctctgcc gttcagttaa aaatgccgga tacagcgttg atggcgggat ggcggaagag      360
tgcatcgtgg tcgccgatta cgcggtaaaa gtgccagatg gtctggactc ggcggcggcc      420
agcagcatta cctgtgcggg agtcaccacc tacaaagccg ttaagctgtc aaaaattcgt      480
ccagggcagt ggattgctat ctacggtctt ggcggtctgg gtaacctcgc cctgcaatac      540
gcgaagaatg tctttaacgc caaagtgatc gccattgatg tcaatgatga gcagttaaaa      600
ctggcaaccg aaatgggcgc agatttagcg attaactcac acaccgaaga cgccgccaaa      660
attgtgcagg agaaaactgg tggcgctcac gctgcggtgg taacagcggt agctaaagct      720
gcgtttaact cggcagttga tgctgtccgt gcaggcggtc gtgttgtggc tgtcggtcta      780
ccgccggagt ctatgagcct ggatatccca cgtcttgtgc tggatggtat tgaagtggtc      840
ggttcgctgg tcggcacgcg ccaggattta actgaagcct ccagtttgc cgccgaaggt      900
aaagtggtgc cgaaagtcgc cctgcgtccg ttagcggaca tcaacaccat ctttactgag      960
atggaagaag gcaaaatccg tggccgcatg gtgattgatt ccgtcacta a                1011
```

```
<210> SEQ ID NO 4
<211> LENGTH: 1024
<212> TYPE: DNA
<213> ORGANISM: Escherichia coli

<400> SEQUENCE: 4
agatcaaagc tgttggtgca tattccgcta acaaccact  tgaaccgatg gatatcaccc       60
ggcgtgaacc gggaccgaat gatgtcaaaa tcgaaatcgc ttactgtggc gtttgccatt      120
ccgatctcca ccaggtccgt tccgagtggg cgggacggt ttacccctgc gtgccgggtc      180
atgaaattgt ggggcgtgtg gtagccgttg gtgatcaggt agaaaaatat gcgccgggcg      240
atctggtcgg tgtcggctgc attgtcgaca gttgtaaaca ttgcgaagag tgtgaagacg      300
ggttggaaaa ctactgtgat cacatgaccg gcacctataa ctcgccgacg ccggacgaac      360
cgggccatac tctgggcggc tactcacaac agatcgtcgt tcatgagcga tatgttctgc      420
gtattcgtca cccgcaagag cagctggcgg cgtggctcc tttgttgtgt gcagggatca      480
ccacgtattc gccgctacgt cactggcagg ccgggccggg taaaaaagtg gcgtggtcg      540
gcatcggcgg tctgggacat atggggatta agctggccca cgcgatgggg gcacatgtgg      600
tggcatttac cacttctgag gcaaaacgcg aagcggcaaa agccctgggg ccgatgaag      660
ttgttaactc acgcaatgcc gatgagatgg cggctcatct gaagagtttc gatttcattt      720
tgaatacagt agctgcgcca cataatctcg acgattttac caccttgctg aagcgtgatg      780
gcaccatgac gctggttggt gcgcctgcga caccgcataa atcgccggaa gttttcaacc      840
tgatcatgaa acgccgtgcg atagccggtt ctatgattgg cggcattcca gaaactcagg      900
agatgctcga ttttgcgcc gaacatggca tcgtggctga tatagagatg attcgggccg      960
atcaaattaa tgaagcctat gagcgaatgc tgcgcggtga tgtgaaatat cgttttgtta     1020
tcga                                                                  1024
```

```
<210> SEQ ID NO 5
<211> LENGTH: 1098
<212> TYPE: DNA
<213> ORGANISM: Escherichia coli

<400> SEQUENCE: 5
atgtcatctg aaaaactgta ttccccactg aaagtgggcg cgatcacggc ggcaaaccgt       60
attttatgg caccgctgac gcgtctgcgc agtattgaac cgggtgacat tcctacccg       120
```

```
ttgatggcgg aatactatcg ccaacgtgcc agtgccggtt tgattattag tgaagccacg      180
caaatttctg cccaggcaaa aggatatgca ggtgcgcctg gcatccatag tccggagcaa      240
attgccgcat ggaaaaaaat caccgctggc gttcatgctg aaaatggtca tatggccgtg      300
cagctgtggc acaccggacg catttctcac gccagcctgc aacctggcgg tcaggcaccg      360
gtagcgcctt cagcacttag cgcgggaaca cgtacttctc tgcgcgatga aaatggtcag      420
gcgatccgtg ttgaaacatc catgccgcgt gcgcttgaac tggaagagat tccaggtatc      480
gtcaatgatt tccgtcaggc cattgctaac gcgcgtgaag ccggttttga tctggtagag      540
ctccactctg ctcacggtta tttgctgcat cagttccttt ctccttcttc aaaccatcgt      600
accgatcagt acggcggcag cgtggaaaat cgcgcacgtt tggtactgga agtggtcgat      660
gccgggattg aagaatgggg tgccgatcgc attggcattc gcgtttcgcc aatcggtact      720
ttccagaaca cagataacgg cccgaatgaa gaagccgatg cactgtatct gattgaacaa      780
ctgggtaaac gcggcattgc ttatctgcat atgtcagaac cagattgggc ggggggtgaa      840
ccgtatactg atgcgttccg cgaaaaagta cgcgcccgtt ccacggtcc gattatcggc       900 gcaggtgcat acacagtaga aaagctgaa acgctgatcg gcaaagggtt aattgatgcg       960
gtggcatttg tcgtgactg gattgcgaac ccggatctgg tcgcccgctt gcagcgcaaa      1020
gctgagctta acccacagcg tgccgaaagt ttctacggtg gcggcgcgga aggctatacc      1080
gattacccga cgttgtaa                                                    1098

<210> SEQ ID NO 6
<211> LENGTH: 18
<212> TYPE: DNA
<213> ORGANISM: Artificial Sequence
<220> FEATURE:
<223> OTHER INFORMATION: adhEF1

<400> SEQUENCE: 6
tgtgcagagg gcggaggc                                                      18

<210> SEQ ID NO 7
<211> LENGTH: 24
<212> TYPE: DNA
<213> ORGANISM: Artificial Sequence
<220> FEATURE:
<223> OTHER INFORMATION: adheR1

<400> SEQUENCE: 7
atgctgaaag gtgtcagctt tgca                                               24

<210> SEQ ID NO 8
<211> LENGTH: 22
<212> TYPE: DNA
<213> ORGANISM: Artificial Sequence
<220> FEATURE:
<223> OTHER INFORMATION: yqdhDF1

<400> SEQUENCE: 8
atccgccagc aagcggcaaa tc                                                 22

<210> SEQ ID NO 9
<211> LENGTH: 20
<212> TYPE: DNA
<213> ORGANISM: Artificial Sequence
<220> FEATURE:
<223> OTHER INFORMATION: yqhDR1
```

```
<400> SEQUENCE: 9
ccgcggcggt atcaatcgag                                               20

<210> SEQ ID NO 10
<211> LENGTH: 21
<212> TYPE: DNA
<213> ORGANISM: Artificial Sequence
<220> FEATURE:
<223> OTHER INFORMATION: adhPF1

<400> SEQUENCE: 10
aggcgtggcg gtgaaaacct c                                             21

<210> SEQ ID NO 11
<211> LENGTH: 19
<212> TYPE: DNA
<213> ORGANISM: Artificial Sequence
<220> FEATURE:
<223> OTHER INFORMATION: adhPR1

<400> SEQUENCE: 11
ctggcaaact cgcgcaggc                                                19

<210> SEQ ID NO 12
<211> LENGTH: 23
<212> TYPE: DNA
<213> ORGANISM: Artificial Sequence
<220> FEATURE:
<223> OTHER INFORMATION: yahKF1

<400> SEQUENCE: 12
tgagtgtgtc ggcagaaatg gac                                           23

<210> SEQ ID NO 13
<211> LENGTH: 26
<212> TYPE: DNA
<213> ORGANISM: Artificial Sequence
<220> FEATURE:
<223> OTHER INFORMATION: yahKR1

<400> SEQUENCE: 13
gtatgctttg ttgcgtatat ggcatc                                        26

<210> SEQ ID NO 14
<211> LENGTH: 25
<212> TYPE: DNA
<213> ORGANISM: Artificial Sequence
<220> FEATURE:
<223> OTHER INFORMATION: nemAF1

<400> SEQUENCE: 14
ccattgttta accttttgtg gcgaa                                         25

<210> SEQ ID NO 15
<211> LENGTH: 24
<212> TYPE: DNA
<213> ORGANISM: Artificial Sequence
<220> FEATURE:
<223> OTHER INFORMATION: nemAR1

<400> SEQUENCE: 15
atttgtattc cgggttttcg ctgg                                          24

<210> SEQ ID NO 16
<211> LENGTH: 891
```

```
<212> TYPE: PRT
<213> ORGANISM: Escherichia coli

<400> SEQUENCE: 16
```

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Leu Ala Ala Asp Ala Arg Ile Pro
        35                  40                  45

Leu Ala Lys Met Ala Val Ala Glu Ser Gly Met Gly Ile Val Glu Asp
        50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Asp Asp Thr Phe Gly
                85                  90                  95

Thr Ile Thr Ile Ala Glu Pro Ile Gly Ile Ile Cys Gly Ile Val Pro
                100                 105                 110

Thr Thr Asn Pro Thr Ser Thr Ala Ile Phe Lys Ser Leu Ile Ser Leu
            115                 120                 125

Lys Thr Arg Asn Ala Ile Ile Phe Ser Pro His Pro Arg Ala Lys Asp
130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
        275                 280                 285

Asn Gly Ala Leu Asn Ala Ala Ile Val Gly Gln Pro Ala Tyr Lys Ile
    290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
                325                 330                 335

Leu Ser Pro Thr Leu Ala Met Tyr Arg Ala Lys Asp Phe Glu Asp Ala
            340                 345                 350

Val Glu Lys Ala Glu Lys Leu Val Ala Met Gly Gly Ile Gly His Thr
        355                 360                 365

Ser Cys Leu Tyr Thr Asp Gln Asp Asn Gln Pro Ala Arg Val Ser Tyr
    370                 375                 380

Phe Gly Gln Lys Met Lys Thr Ala Arg Ile Leu Ile Asn Thr Pro Ala
385                 390                 395                 400

```
Ser Gln Gly Gly Ile Gly Asp Leu Tyr Asn Phe Lys Leu Ala Pro Ser
            405                 410                 415

Leu Thr Leu Gly Cys Gly Ser Trp Gly Gly Asn Ser Ile Ser Glu Asn
            420                 425                 430

Val Gly Pro Lys His Leu Ile Asn Lys Thr Val Ala Lys Arg Ala
            435                 440                 445

Glu Asn Met Leu Trp His Lys Leu Pro Lys Ser Ile Tyr Phe Arg Arg
450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
            485                 490                 495

Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
            515                 520                 525

Ala Glu Leu Ala Asn Ser Phe Lys Pro Asp Val Ile Ala Leu Gly
            530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575

Arg Lys Arg Ile Tyr Lys Phe Pro Lys Met Gly Val Lys Ala Lys Met
                580                 585                 590

Ile Ala Val Thr Thr Thr Ser Gly Thr Gly Ser Glu Val Thr Pro Phe
            595                 600                 605

Ala Val Val Thr Asp Asp Ala Thr Gly Gln Lys Tyr Pro Leu Ala Asp
            610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
                660                 665                 670

Gly Gln Ala Leu Gln Ala Leu Lys Leu Leu Lys Glu Tyr Leu Pro Ala
            675                 680                 685

Ser Tyr His Glu Gly Ser Lys Asn Pro Val Ala Arg Glu Arg Val His
            690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
                740                 745                 750

Ala Asn Asp Asn Pro Thr Lys Gln Thr Ala Phe Ser Gln Tyr Asp Arg
            755                 760                 765

Pro Gln Ala Arg Arg Arg Tyr Ala Glu Ile Ala Asp His Leu Gly Leu
            770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815
```

-continued

Glu Ala Gly Val Gln Glu Ala Asp Phe Leu Ala Asn Val Asp Lys Leu
                820                 825                 830

Ser Glu Asp Ala Phe Asp Asp Gln Cys Thr Gly Ala Asn Pro Arg Tyr
        835                 840                 845

Pro Leu Ile Ser Glu Leu Lys Gln Ile Leu Leu Asp Thr Tyr Tyr Gly
        850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
                885                 890

<210> SEQ ID NO 17
<211> LENGTH: 387
<212> TYPE: PRT
<213> ORGANISM: Escherichia coli

<400> SEQUENCE: 17

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
                20                  25                  30

Leu Ile Thr Tyr Gly Gly Gly Ser Val Lys Lys Thr Gly Val Leu Asp
            35                  40                  45

Gln Val Leu Asp Ala Leu Lys Gly Met Asp Val Leu Glu Phe Gly Gly
        50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
                100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

```
Leu Gln Tyr Ala Glu Arg Val Trp Asn Ile Thr Glu Gly Ser Asp Asp
305                 310                 315                 320

Glu Arg Ile Asp Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
                340                 345                 350

Ile Pro Ala Leu Leu Lys Lys Leu Glu Glu His Gly Met Thr Gln Leu
                355                 360                 365

Gly Glu Asn His Asp Ile Thr Leu Asp Val Ser Arg Arg Ile Tyr Glu
370                 375                 380

Ala Ala Arg
385

<210> SEQ ID NO 18
<211> LENGTH: 336
<212> TYPE: PRT
<213> ORGANISM: Escherichia coli

<400> SEQUENCE: 18

Met Lys Ala Ala Val Val Thr Lys Asp His Val Asp Val Thr Tyr
1               5                   10                  15

Lys Thr Leu Arg Ser Leu Lys His Gly Glu Ala Leu Leu Lys Met Glu
                20                  25                  30

Cys Cys Gly Val Cys His Thr Asp Leu His Val Lys Asn Gly Asp Phe
            35                  40                  45

Gly Asp Lys Thr Gly Val Ile Leu Gly His Glu Gly Ile Gly Val Val
        50                  55                  60

Ala Glu Val Gly Pro Gly Val Thr Ser Leu Lys Pro Gly Asp Arg Ala
65                  70                  75                  80

Ser Val Ala Trp Phe Tyr Glu Gly Cys Gly His Cys Glu Tyr Cys Asn
                85                  90                  95

Ser Gly Asn Glu Thr Leu Cys Arg Ser Val Lys Asn Ala Gly Tyr Ser
                100                 105                 110

Val Asp Gly Gly Met Ala Glu Glu Cys Ile Val Val Ala Asp Tyr Ala
            115                 120                 125

Val Lys Val Pro Asp Gly Leu Asp Ser Ala Ala Ser Ser Ile Thr
130                 135                 140

Cys Ala Gly Val Thr Thr Tyr Lys Ala Val Lys Leu Ser Lys Ile Arg
145                 150                 155                 160

Pro Gly Gln Trp Ile Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
                180                 185                 190

Asp Val Asn Asp Glu Gln Leu Lys Leu Ala Thr Glu Met Gly Ala Asp
            195                 200                 205

Leu Ala Ile Asn Ser His Thr Glu Asp Ala Ala Lys Ile Val Gln Glu
210                 215                 220

Lys Thr Gly Gly Ala His Ala Ala Val Val Thr Ala Val Ala Lys Ala
225                 230                 235                 240

Ala Phe Asn Ser Ala Val Asp Ala Val Arg Ala Gly Gly Arg Val Val
                245                 250                 255

Ala Val Gly Leu Pro Pro Glu Ser Met Ser Leu Asp Ile Pro Arg Leu
            260                 265                 270

Val Leu Asp Gly Ile Glu Val Val Gly Ser Leu Val Gly Thr Arg Gln
```

```
                    275                 280                 285
Asp Leu Thr Glu Ala Phe Gln Phe Ala Ala Glu Gly Lys Val Val Pro
    290                 295                 300

Lys Val Ala Leu Arg Pro Leu Ala Asp Ile Asn Thr Ile Phe Thr Glu
305                 310                 315                 320

Met Glu Glu Gly Lys Ile Arg Gly Arg Met Val Ile Asp Phe Arg His
                325                 330                 335

<210> SEQ ID NO 19
<211> LENGTH: 347
<212> TYPE: PRT
<213> ORGANISM: Escherichia coli

<400> SEQUENCE: 19

Met Lys Ile Lys Ala Val Gly Ala Tyr Ser Ala Lys Gln Pro Leu Glu
1               5                   10                  15

Pro Met Asp Ile Thr Arg Arg Glu Pro Gly Pro Asn Asp Val Lys Ile
                20                  25                  30

Glu Ile Ala Tyr Cys Gly Val Cys His Ser Asp Leu His Gln Val Arg
            35                  40                  45

Ser Glu Trp Ala Gly Thr Val Tyr Pro Cys Val Pro Gly His Glu Ile
    50                  55                  60

Val Gly Arg Val Val Ala Val Gly Asp Gln Val Glu Lys Tyr Ala Pro
65                  70                  75                  80

Gly Asp Leu Val Gly Val Gly Cys Ile Val Asp Ser Cys Lys His Cys
                85                  90                  95

Glu Glu Cys Glu Asp Gly Leu Glu Asn Tyr Cys Asp His Met Thr Gly
            100                 105                 110

Thr Tyr Asn Ser Pro Thr Pro Asp Glu Pro Gly His Thr Leu Gly Gly
        115                 120                 125

Tyr Ser Gln Gln Ile Val Val His Glu Arg Tyr Val Leu Arg Ile Arg
    130                 135                 140

His Pro Gln Glu Gln Leu Ala Ala Val Ala Pro Leu Leu Cys Ala Gly
145                 150                 155                 160

Ile Thr Thr Tyr Ser Pro Leu Arg His Trp Gln Ala Gly Pro Gly Lys
                165                 170                 175

Lys Val Gly Val Val Gly Ile Gly Gly Leu Gly His Met Gly Ile Lys
            180                 185                 190

Leu Ala His Ala Met Gly Ala His Val Val Ala Phe Thr Thr Ser Glu
        195                 200                 205

Ala Lys Arg Glu Ala Ala Lys Ala Leu Gly Ala Asp Glu Val Val Asn
    210                 215                 220

Ser Arg Asn Ala Asp Glu Met Ala Ala His Leu Lys Ser Phe Asp Phe
225                 230                 235                 240

Ile Leu Asn Thr Val Ala Ala Pro His Asn Leu Asp Asp Phe Thr Thr
                245                 250                 255

Leu Leu Lys Arg Asp Gly Thr Met Thr Leu Val Gly Ala Pro Ala Thr
            260                 265                 270

Pro His Lys Ser Pro Glu Val Phe Asn Leu Ile Met Lys Arg Arg Ala
        275                 280                 285

Ile Ala Gly Ser Met Ile Gly Gly Ile Pro Glu Thr Gln Glu Met Leu
    290                 295                 300

Asp Phe Cys Ala Glu His Gly Ile Val Ala Asp Ile Glu Met Ile Arg
305                 310                 315                 320
```

Ala Asp Gln Ile Asn Glu Ala Tyr Glu Arg Met Leu Arg Gly Asp Val
            325                 330                 335

Lys Tyr Arg Phe Val Ile Asp Asn Arg Thr Leu
            340                 345

<210> SEQ ID NO 20
<211> LENGTH: 365
<212> TYPE: PRT
<213> ORGANISM: Escherichia coli

<400> SEQUENCE: 20

Met Ser Ser Glu Lys Leu Tyr Ser Pro Leu Lys Val Gly Ala Ile Thr
1               5                   10                  15

Ala Ala Asn Arg Ile Phe Met Ala Pro Leu Thr Arg Leu Arg Ser Ile
            20                  25                  30

Glu Pro Gly Asp Ile Pro Thr Pro Leu Met Ala Glu Tyr Tyr Arg Gln
        35                  40                  45

Arg Ala Ser Ala Gly Leu Ile Ile Ser Glu Ala Thr Gln Ile Ser Ala
50                  55                  60

Gln Ala Lys Gly Tyr Ala Gly Ala Pro Gly Ile His Ser Pro Glu Gln
65                  70                  75                  80

Ile Ala Ala Trp Lys Lys Ile Thr Ala Gly Val His Ala Glu Asn Gly
                85                  90                  95

His Met Ala Val Gln Leu Trp His Thr Gly Arg Ile Ser His Ala Ser
            100                 105                 110

Leu Gln Pro Gly Gly Gln Ala Pro Val Ala Pro Ser Ala Leu Ser Ala
        115                 120                 125

Gly Thr Arg Thr Ser Leu Arg Asp Glu Asn Gly Gln Ala Ile Arg Val
130                 135                 140

Glu Thr Ser Met Pro Arg Ala Leu Glu Leu Glu Ile Pro Gly Ile
145                 150                 155                 160

Val Asn Asp Phe Arg Gln Ala Ile Ala Asn Ala Arg Glu Ala Gly Phe
                165                 170                 175

Asp Leu Val Glu Leu His Ser Ala His Gly Tyr Leu Leu His Gln Phe
            180                 185                 190

Leu Ser Pro Ser Ser Asn His Arg Thr Asp Gln Tyr Gly Gly Ser Val
        195                 200                 205

Glu Asn Arg Ala Arg Leu Val Leu Glu Val Val Asp Ala Gly Ile Glu
210                 215                 220

Glu Trp Gly Ala Asp Arg Ile Gly Ile Arg Val Ser Pro Ile Gly Thr
225                 230                 235                 240

Phe Gln Asn Thr Asp Asn Gly Pro Asn Glu Glu Ala Asp Ala Leu Tyr
                245                 250                 255

Leu Ile Glu Gln Leu Gly Lys Arg Gly Ile Ala Tyr Leu His Met Ser
            260                 265                 270

Glu Pro Asp Trp Ala Gly Gly Glu Pro Tyr Thr Asp Ala Phe Arg Glu
        275                 280                 285

Lys Val Arg Ala Arg Phe His Gly Pro Ile Ile Gly Ala Gly Ala Tyr
290                 295                 300

Thr Val Glu Lys Ala Glu Thr Leu Ile Gly Lys Gly Leu Ile Asp Ala
305                 310                 315                 320

Val Ala Phe Gly Arg Asp Trp Ile Ala Asn Pro Asp Leu Val Ala Arg
                325                 330                 335

Leu Gln Arg Lys Ala Glu Leu Asn Pro Gln Arg Ala Glu Ser Phe Tyr
            340                 345                 350

-continued

```
Gly Gly Gly Ala Glu Gly Tyr Thr Asp Tyr Pro Thr Leu
            355                 360             365
```